(12) United States Patent
Newton et al.

(10) Patent No.: US 11,642,176 B2
(45) Date of Patent: May 9, 2023

(54) CATHETER LOCATION DETERMINATION IN PAEDIATRIC PATIENTS

(71) Applicant: Navi Medical Technologies Pty Ltd, Box Hill (AU)

(72) Inventors: Alexander Newton, Prahan (AU); Bradley Bergmann, Bondi (AU); Mubin Yousuf, Cairnlea (AU); Christiane Theda, Box Hill (AU); Shing Yue Sheung, Balwyn (AU); Wei Xin Sue, Preston (AU)

(73) Assignee: NAVI MEDICAL TECHNOLOGIES PTY LTD, Victoria (AU)

( * ) Notice: Subject to any disclaimer, the term of this patent is extended or adjusted under 35 U.S.C. 154(b) by 259 days.

(21) Appl. No.: 16/757,316

(22) PCT Filed: Oct. 19, 2018

(86) PCT No.: PCT/AU2018/051142
§ 371 (c)(1),
(2) Date: Apr. 17, 2020

(87) PCT Pub. No.: WO2019/075529
PCT Pub. Date: Apr. 25, 2019

(65) Prior Publication Data
US 2021/0259778 A1   Aug. 26, 2021

Related U.S. Application Data

(60) Provisional application No. 62/574,403, filed on Oct. 19, 2017.

(51) Int. Cl.
*A61B 34/20* (2016.01)
*G06N 20/00* (2019.01)
(Continued)

(52) U.S. Cl.
CPC .............. *A61B 34/20* (2016.02); *A61B 5/061* (2013.01); *A61B 5/29* (2021.01); *A61B 5/352* (2021.01);
(Continued)

(58) Field of Classification Search
CPC ......... A61B 5/061; A61B 5/29; A61B 5/7221; A61B 34/20; A61B 5/6852; A61B 5/353;
(Continued)

(56) References Cited

U.S. PATENT DOCUMENTS 9,440,047 B1    9/2016  Elberse et al.
9,445,746 B1 *  9/2016  Elberse .................. A61B 5/283
(Continued)

FOREIGN PATENT DOCUMENTS

WO     WO 2017/122117 A1     7/2017

OTHER PUBLICATIONS

International Search Report and Written Opinion dated Jan. 31, 2019 in International Application No. PCT/AU2018/051142 (12 pages).
(Continued)

*Primary Examiner* — Brenda C Bernardi
(74) *Attorney, Agent, or Firm* — Orrick, Herrington & Sutcliffe LLP

(57) ABSTRACT

When inserting a catheter or other medical equipment into a child or adolescent or other paediatric patient, ECG signals may be recorded from the catheter and the location of the catheter determined by analysing the ECG signals. A signal processor and user interface may receive recorded signals in real-time from the catheter while the catheter is inserted into the paediatric patient. The signal processor may analyse the ECG signals to determine the location of the catheter in the paediatric patient. The user interface may display the location of the catheter and other pertinent information to a user
(Continued)

while the user is inserting the catheter. One method for determining the location may include determining R-wave and P-wave peaks of the ECG signal and determining the location from an average location of the R-wave and P-wave peaks in the ECG signal.

6 Claims, 23 Drawing Sheets

(51) Int. Cl.
    *A61B 5/353*     (2021.01)
    *A61B 5/352*     (2021.01)
    *A61B 5/29*     (2021.01)
    *A61B 5/06*     (2006.01)
    *A61B 5/00*     (2006.01)
    *A61M 25/00*     (2006.01)

(52) U.S. Cl.
    CPC ............ *A61B 5/353* (2021.01); *A61B 5/7203* (2013.01); *A61M 25/0017* (2013.01); *G06N 20/00* (2019.01); *A61B 2503/045* (2013.01)

(58) Field of Classification Search
    CPC ......... A61B 5/283; A61B 5/316; A61B 5/352; A61B 5/7267; A61B 5/349; A61B 5/743; A61B 5/7203; A61B 5/7257; A61B 2503/045; G06N 20/00; A61M 25/0017
    See application file for complete search history.

(56) References Cited

U.S. PATENT DOCUMENTS

| | | | | |
|---|---|---|---|---|
| 9,877,665 | B2* | 1/2018 | Elberse | A61B 5/339 |
| 2010/0318026 | A1* | 12/2010 | Grunwald | A61B 5/283 |
| | | | | 604/95.05 |
| 2016/0278869 | A1* | 9/2016 | Grunwald | A61B 8/4472 |
| 2016/0346512 | A1* | 12/2016 | Elberse | A61B 5/318 |
| 2017/0035323 | A1* | 2/2017 | Elberse | A61B 5/349 |
| 2018/0344190 | A1* | 12/2018 | Roy | A61B 5/283 |

OTHER PUBLICATIONS

International Preliminary Report on Patentability under Chapter II dated Sep. 12, 2019 in International Application No. PCT/AU2018/051142 (19 pages).

Perin, G, et al. "Defining central venous line position in children: tips for the tip" The Journal of vascular access, vol. 16, No. 2, pp. 77-86, Mar. 2015.

Pittiruti M, et al. "The electrocardiographic method for positioning the tip of central venous catheters" The Journal of vascular access, vol. 12, No. 4, pp. 280-291, 2011.

Rossetti F, et al. "The intracavitary ECG method for positioning the tip of central venous access devices in pediatric patients: results of an Italian multicenter study" The Journal of vascular access, vol. 16, No. 2, pp. 137-143, Mar. 2015.

Tsui, BC, et al. "Umbilical vein catheterization under electrocardiogram guidance" Pediatric Anesthesia, vol. 15, No. 4, pp. 297-300, Apr. 2005.

Stocker M, et al. "Arterielle und zentralvenöse Katheter bei Neugeborenen und Säuglingen" Der Anaesthesist, vol. 55, No. 8, pp. 873-882, Aug. 1, 2006. (English translation of abstract only).

Extended European Search Report, Application No. 18 867 348.7, dated Jul. 22, 2021.

* cited by examiner f1 → boundary around points representing liver
f2 → boundary around points representing IVC
1-(f1+f2) → points representing other locations

CATHETER LOCATION DETERMINATION IN PAEDIATRIC PATIENTS

CROSS-REFERENCE TO RELATED PATENT APPLICATIONS

This patent application claims priority from U.S. provisional patent application No. 62/574,403, filed 19 Oct. 2017.

FIELD OF THE DISCLOSURE

The instant disclosure relates to medical devices. More specifically, portions of this disclosure relate to processing signals to determine a location of a catheter in paediatric patients. Examples of applications of this disclosure include determining a location of an Umbilical Venous Catheter in a newborn baby or Central Venous Catheter in a child or adolescent.

BACKGROUND

Central venous catheters (CVCs) are used to administer fluids and medication to paediatric patients, such as newborn babies, infants, children and adolescents. For newborn babies, also referred to as neonates the type of CVC used is referred to as an umbilical venous catheter (UVC) as this can be inserted through the umbilical vein, which remains viable for cannulation at least until approximately one week after birth. In the following description references to CVC should be understood to include UVCs. The conventional use of CVCs involves a blind procedure to insert the catheter towards the inferior vena cava or superior vena cava either through the umbilicus or through peripheral (via veins in the limbs) or femoral or central access (via veins in the neck region) towards the superior vena cava. However, blindly inserting the catheter can result in incorrect placement of the catheter, ineffective treatments using the catheter, or physical injury to internal organs from the penetration of the catheter. In addition, catheter tip mis-location due to migration of the catheter after insertion occurs in a large number of paediatric patients catheterised.

SUMMARY

According to one aspect there is a provided method, comprising: receiving an electrocardiogram (ECG) signal from a tip of a catheter inserted in a paediatric patient, determining R-wave peaks in the ECG signal; determining P-wave peaks in the ECG signal; and determining a location of the catheter in the neonate based, at least in part, on the P-wave peaks and the R-wave peaks using a trained machine-learning engine.

In an embodiment, the step of determining R-wave peaks comprises: determining an initial R-wave peak based on determining a largest peak in the ECG signal within a first time window, wherein the first time window has a first duration based on a usual heart rate of the paediatric patient; determining a second time window starting at the initial R-wave peak and having a second duration based on the usual heart rate of the paediatric patient, the second duration being marginally shorter than the first duration; and determining a subsequent R-wave peak as a first peak in the ECG signal after the second time window.

In an embodiment, the second duration of the second time window is approximately equal to a half of a usual QRS duration less than a RR interval, wherein the QRS duration is from a beginning of a QRS complex to an end of the QRS complex of the electrocardiogram (ECG) signal, and wherein the RR interval is a duration from the initial R-wave peak to the subsequent R-wave peak.

In another embodiment, the step of determining R-wave peaks comprises: a) determining a first maximum value in the ECG signal during a first time window, the first time window having a duration based on patient heart rate; b) sliding the first time window to a second time window later in time in the ECG signal; c) determining a second maximum value in the ECG signal during the second time window; d) determining a difference between the first maximum value and the second maximum value; e) performing threshold analysis of the difference and where the difference does not meet threshold criteria, repeating steps b) to e), and where the difference does meet threshold criteria determining an R-peak corresponding to a maximum of the first maximum value and the second maximum value, and f) repeating steps a) to e) to determine a subsequent R-peak. The threshold criteria can include time difference relative to time of previous maximum value within the ECG signal.

In some embodiments, the step of determining P-wave peaks comprises determining an initial P-wave peak by determining a largest peak in a third time window prior to the subsequent R-wave peak, wherein the third time window has a third duration based on a PR-interval value for the paediatric patient. In an example the third duration for the third time window can be determined based on known usual PR interval characteristics for based on age of the patient. In another example, the third duration for the third time window can be determined based on measuring the PR interval from a surface ECG signal for the patient.

Some embodiments further determine additional subsequent R-wave peaks in the ECG signal. Some embodiments further determine additional subsequent P-wave peaks within periods of time equal to the third duration prior to each of the additional subsequent R-wave peaks in the ECG signal. The method can further comprise: determining a first average of an amplitude of the additional subsequent R-wave peaks; and determining a second average of an amplitude of the additional subsequent P-wave peaks, wherein the determining a location of the catheter is based, at least in part, on the first average and the second average. Some embodiments further comprise: receiving a baseline ECG signal from a skin surface of the patient; normalizing the additional subsequent R-wave peaks based on the baseline ECG signal; and normalizing the additional subsequent P-wave peaks based on the baseline ECG signal, wherein the location is based on the normalized additional subsequent R-wave peaks and the normalized additional subsequent P-wave peaks. Some embodiments further comprise: determining a third average of an amplitude of R-wave peaks in the baseline ECG signal; determining a fourth average of an amplitude of P-wave peaks in the baseline ECG signal, wherein the step of normalizing the additional subsequent R-wave peaks comprises dividing the first average by the third average, and wherein the step of normalizing the additional subsequent P-wave peaks comprises dividing the second average by the fourth average.

In some embodiments, the step of determining the location using a trained machine-learning algorithm utilises R-wave peak and P-wave peak values. In some embodiments, the step of determining the location using a trained machine-learning engine utilises ratios of R-wave peak and P-wave peak values. In some embodiments, the step of determining the location using a trained machine-learning engine utilises the normalised R-wave peak values and normalised P-wave peak values. In some embodiments, the step of determining the location using a trained machine-learning engine comprises the machine learning engine using at least one of an artificial neural network algorithm, a deep learning algorithm, a Bayesian network algorithm, a decision tree learning algorithm, and a rule-based learning algorithm trained using labelled clinical data.

Any of the above methods can also comprise an initial step of determining intravascular ECG signal quality by performing a fast Fourier transform (FFT) on a sample of the received intravascular ECG signal, and a signal quality determination module analysing the FFT to determining whether the signal is of adequate for catheter tip location determination, and trigger an alert to an operator where the signal quality is not adequate. In an embodiment the signal quality is based on comparison of the FFT with threshold criteria. In an embodiment, the signal quality is determined by a trained machine learning engine.

Some embodiments further comprise displaying the location of the catheter in the patient to a user. In an embodiment the step of displaying the location of the catheter comprises any one or more of a plurality of colours, and plurality of shapes, indicating whether the catheter is in a correct final location, whether the catheter is in an incorrect final location, and whether the catheter is neither in a correct nor incorrect final location. In another embodiment displaying the location can further comprise the steps of determining a catheter location zone and displaying a zone indication.

Another aspect provides an apparatus, comprising: a processor configured to perform steps comprising: receiving an electrocardiogram (ECG) signal from a tip of a catheter inserted in a paediatric patient; determining P-wave peaks in the ECG signal; determining R-wave peaks in the ECG signal; and determining a location of the catheter in the paediatric patient based, at least in part, on the P-wave peaks and the R-wave peaks using a trained machine-learning algorithm.

In some embodiments of the apparatus, the processor is configured to determine R-wave peaks by: determining an initial R-wave peak based on determining a largest peak in the ECG signal within a first time window, wherein the first time window has a first duration based on a usual heart rate of the paediatric patient; determining a second time window starting at the initial R-wave peak and having a second duration based on the usual heart rate of the paediatric patient, the second duration being marginally shorter than the first duration; and determining a subsequent R-wave peak as a first peak in the ECG signal after the second time window, and wherein the processor is configured to determine P-wave peaks by: determining an initial P-wave peak by determining a largest peak in a third time window prior to the subsequent R-wave peak, wherein the third time window has a third duration based on a PR-interval value for the paediatric patient.

In some embodiments of the apparatus, the processor is further configured to perform: determining additional subsequent R-wave peaks in the ECG signal; determining additional subsequent P-wave peaks within periods of time equal to the third duration prior to each of the additional subsequent R-wave peaks in the ECG signal; determining a first average of an amplitude of the additional subsequent R-wave peaks; and determining a second average of an amplitude of the additional subsequent P-wave peaks, wherein the location is based, at least in part, on the first average and the second average.

In some embodiments of the apparatus, the processor is further configured to perform: receiving a baseline ECG signal from a skin surface of the paediatric patient; determining a third average of an amplitude of R-wave peaks in the baseline ECG signal; and determining a fourth average of P-wave peaks in the baseline ECG signal, wherein the location is based on the first average, the second average, the third average, and the fourth average.

In some embodiments of the apparatus, the processor is configured to determine R-wave peaks by: a) determining a first maximum value in the ECG signal during a first time window, the first time window having a duration based on patient heart rate; b) sliding the first time window to a second time window later in time in the ECG signal; c) determining a second maximum value in the ECG signal during the second time window; d) determining a difference between the first maximum value and the second maximum value; e) performing threshold analysis of the difference and where the difference does not meet threshold criteria, repeating steps b) to e), and where the difference does not meet the threshold criteria determining a first R-peak corresponding to a maximum of the first maximum value and the second maximum value, and f) repeating steps a) to e) to determine a subsequent R-peak. The threshold criteria can include time difference relative to time of previous maximum value within the ECG signal.

Some embodiments of the apparatus further comprising a display coupled to the processor, wherein the processor is configured to output to the display the location of the catheter in the paediatric patient to a user and the ECG signal alongside the location. In some embodiments the processor is configured to output to the display any one or more of a plurality of colours, and a plurality of shapes, indicating any one or more of: the quality of the ECG signal; a zone indication; whether the catheter is in a correct final location; whether the catheter is in an incorrect final location; and whether the catheter is neither in a correct nor incorrect final location.

Some embodiments of the further comprise a catheter adapter, wherein the catheter adapter comprises a three-way connection configured to provide a physical link between a catheter, a saline-flushing syringe, and an electrical connector between the lead and the processor.

In certain embodiments, determining the R-wave peaks may include determining an initial R-wave peak based on determining the largest peak in the surface electrocardiogram (ECG) signal within a first time window, wherein the first time window has a first duration based on a usual heart rate of the neonate; determining a second time window starting at the initial R-wave peak and having a second duration based on the usual heart rate of the neonate; and determining a subsequent R-wave peak as a first peak in the electrocardiogram (ECG) signal after the second time window. The duration of the second time window may be approximately equal to a half of a usual QRS duration (defined as time from start of Q wave to end of S wave) less than a RR interval, wherein the QRS duration is a predetermined period for a neonate from a beginning of a QRS complex to an end of the QRS complex of the electrocardiogram (ECG) signal, and wherein the RR interval is a duration from the initial R-wave peak to the subsequent R-wave peak. The predetermined periods may be based on the usual heart rate of a neonate.

In certain embodiments, determining the P-wave peaks may include determining an initial P-wave peak by determining a largest peak in a third time window prior to the subsequent R-wave peak, wherein the third time window has a third duration based on a predetermined usual PR-interval (defined as time from the start of P-wave until the beginning of the QRS complex) value for the neonate.

In some embodiments, the step of determining a location of the catheter may include determining a first average intensity of R-wave peaks in the buffered ECG signal and determining a second average intensity of P-wave peaks in the buffered ECG signal, and determining the location from the first average and the second average. In one embodiment, these averages may be normalized to a baseline ECG signal by receiving a baseline ECG signal from the skin surface of the neonate; normalizing the R-wave peaks based on the baseline electrocardiogram (ECG) signal; and normalizing the P-wave peaks based on the baseline electrocardiogram (ECG) signal. The normalization may include determining a third average intensity of R-wave peaks in the baseline electrocardiogram (ECG) signal; determining a fourth average intensity of P-wave peaks in the baseline electrocardiogram (ECG) signal; and dividing the first average by the third average and dividing the second average by the fourth average.

Although the location of a catheter is described in the embodiments of this disclosure, the location of other medical equipment or other devices in the human body may be determined from the described techniques for analysing ECG signals. Any measurement of electrical signals within the human body may produce an ECG signal that can be analysed according to the described embodiments.

The term "determining" is used to encompass any process that produces a result, such as a producing a numerical result or producing a signal waveform. Thus, "determining" can include calculating, computing, processing, deriving, investigating, looking up (e.g., looking up in a table, a database or another data structure), ascertaining, and the like. Also, "determining" can include receiving (e.g., receiving information), accessing (e.g., accessing data in a memory), and the like. Furthermore, "determining" can include resolving, selecting, choosing, establishing, identifying, and the like.

The term "signal processing" may refer to the processing and interpretation of signals. Processing of signals may include storage and reconstruction, separation of information from noise, compression, and/or feature extraction. The term "digital signal processing" may refer to the processing, as described above, of digital signals. A digital signal processor (DSP) may be used to perform digital signal processing. Other digital logic circuitry, such as central processing units (CPUs) and graphical processing units (GPUs) may be used to perform digital signal processing. Digital logic circuitry may be used to process analog signals by converting the analog signals to digital signals using an analog-to-digital converter (ADC). A processed digital signal may be returned to an analog signal using a digital-to-analog converter (DAC). A DSP, other digital logic circuitry, or analog circuitry may be used to perform signal processing algorithms described in embodiments of this disclosure.

The foregoing has outlined rather broadly certain features and technical advantages of embodiments of the present invention in order that the detailed description that follows may be better understood. Additional features and advantages will be described hereinafter that form the subject of the claims of the invention. It should be appreciated by those having ordinary skill in the art that the conception and specific embodiment disclosed may be readily utilized as a basis for modifying or designing other structures for carrying out the same or similar purposes. It should also be realized by those having ordinary skill in the art that such equivalent constructions do not depart from the spirit and scope of the invention as set forth in the appended claims. Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

For a more complete understanding of the disclosed system and methods, reference is now made to the following descriptions taken in conjunction with the accompanying drawings.

DETAILED DESCRIPTION

Figure 1:
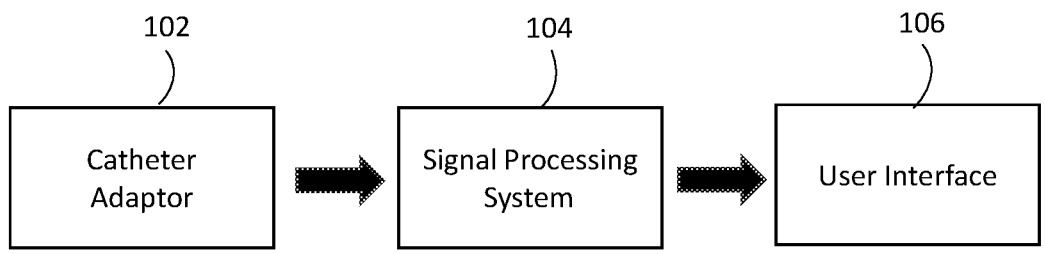
FIG. 1 is a block diagram illustrating a system for providing a catheter location to a user based on an electrical signal obtained from the catheter according to some embodiments of the disclosure.

Aspects of the present disclosure provide methods and systems for receiving an electrocardiogram (ECG) signal from a tip of a catheter inserted in a paediatric patient, determining R-wave peaks in the ECG signal, determining P-wave peaks in the ECG signal, and determining a location of the catheter in the paediatric patient based, at least in part, on the P-wave peaks and the R-wave peaks using a trained machine-learning engine.

The sinoatrial node of the heart creates electrical signals that extend through the human body. An electrocardiogram (ECG) signal is a measurement of these electrical signals from the heart. The ECG can be measured at various places on the human body. In a paediatric patient, for example a neonate, infant, toddler, child or adolescent. In smaller patients such as neonates to toddlers, the distance from the heart to any other part of the body is small relative to the same distance on an adult. As a result, the ECG signal can be easily detectable throughout the patient's thorax. Further there is low latency between intervascular and surface ECG signals due to the small patient size. ECG signals, and neonate and paediatric ECG signals in particular, have certain common characteristics even though every individual's ECG signal is not the same. These characteristics of the ECG signal propagate differently throughout the body. Thus, the location in the body of the ECG measurement may be determined by analysing the ECG signal for these known characteristics.

When inserting a catheter or other medical equipment into a neonate or other patient, ECG signals may be recorded from the catheter tip using a saline column and the location of the catheter determined by analysing the ECG signals. A signal processor and user interface, such as part of a personal computer, may receive monitored ECG signals in real-time from the catheter while the catheter is inserted into the vascular or arterial vessels of a paediatric patient. The signal processor may analyse the ECG signals to determine the location of the catheter in the patient. The user interface may display the location of the catheter and other pertinent information to a user while the user is inserting the catheter, or whether the catheter tip has displaced or 'migrated' from its target location after placement. Thus, the user may use the real-time feedback to guide the catheter to a desired location and prevent unintended injury caused by a wayward catheter or by administering fluids into sub-optimal catheter tip locations due to a migrated catheter.

ECG signals vary from patient to patient creating a challenge to determining location of central catheter using ECG signals, particularly for users who attempt to guide the catheter manually while viewing the monitored ECG signal. In addition, ECG signals vary between paediatric patients and with different ages, due to development of the anatomy, such as changes in the cardiac axis angle. This variation can create significant challenges for younger patients. Significant variation in heartbeat and therefore associated ECG signal continue to vary significantly in paediatric patients from birth until adolescence. The changes are associated with natural growth and development of paediatric patients. The rate of change in heartbeat characteristics and ECG signals varies rapidly for neonates and gradually slows down as the patients get older. However, significant changes can be observed through adolescence well into teenage years (for example 15 to 19) although at a slower rate of change compared to a newborn or toddler, before stabilizing to more regular adult heart beat characteristics. The age at which developmental (growth) based heartbeat changes cease varies from patient to patient, but typically a patient will not attain their adult heartbeat until at least mid to late teenage years. This heartbeat and ECG signal variability in paediatrics is a known problem, with known commercially used ECG based catheter location prediction systems being unreliable with low location prediction accuracy, particularly for very young patients. The methods and systems in accordance with the present disclosure are designed to detect specific characteristics of the ECG signals and use these characteristics to determine location despite the patient-to-patient and age-related variations. Aspects of the disclosed methods utilise characteristics of the monitored ECG signals to compensate for development related variations and inter patient variability. Techniques employed to achieve this compensation include any one or more of ECG signal normalisation, peak averaging, analysis utilising development-based characteristics, modelling, and machine learning based analysis. A model may be used to determine the catheter location from the ECG signal characteristics. The model may be a trained machine-learning algorithm, which can be trained from clinical ECG recordings taken from various locations in patients' bodies labelled with confirmation techniques that may include antero-posterior and lateral x-rays, and ultrasound images.

Characteristics used to determine the catheter location may include analysis of R-wave and P-wave peaks in a surface ECG, and in an intravascular ECG. For a surface ECG, the ECG signal generally includes a P-wave, a QRS-complex, and a T-wave. The P-wave is caused by electrical potentials generated when the atria depolarize and before atrial contraction begins. The QRS-complex is caused by potentials generated when the ventricles depolarize before contraction. The T-wave is caused by the potentials generated as the ventricles recover from depolarization. R-wave and P-wave peaks may be identified in an ECG signal using appropriate time windows. The average intensity (e.g., as represented by an amplitude of the ECG signal at the peak) of the R-wave and P-wave peaks over a recent recording of several R-R periods of the ECG signal may be used to determine the location of the catheter. The PQRST convention is suitable for surface ECG as all peaks in the waveform have known characteristics that make them different from each other. While, in intravascular ECG signals, the characteristics are not prominent and vary based on the catheter location making it difficult to determine the origin of each peak. Therefore, electrophysiologists may use A/V/His conventions (corresponding to atrial origin, ventricular origin, and bundle of His origin) based on the electrode configurations and the catheter location inside to label the peaks. While the exact conventions vary slightly between specific laboratories, the fact that p-waves are originated from the atria and QRS complex originate from the ventricle, can establish a relationship between the surface and intravascular conventions. Hence, sometimes P-waves and A waves and QRS complex and V waves may be used interchangeably.

Figure 10:
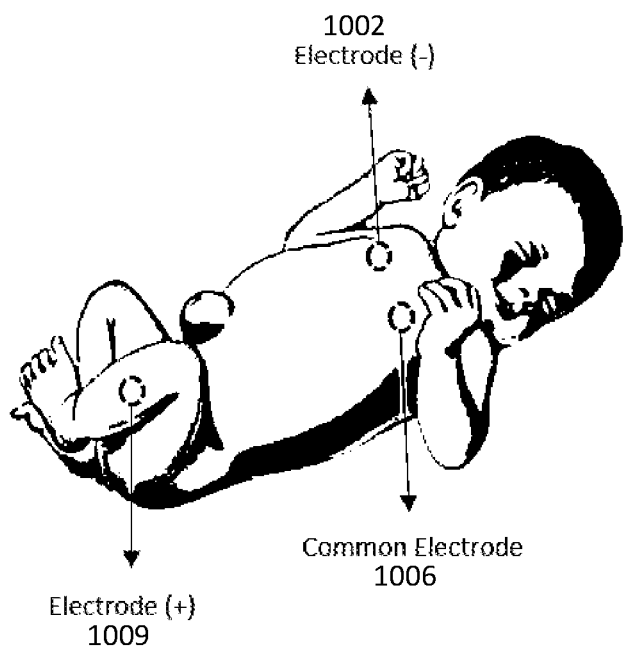
FIG. 10 is an illustration of an example placement of leads on a paediatric patient for recording a baseline ECG signal according to some embodiments of the disclosure.
Figure 11:
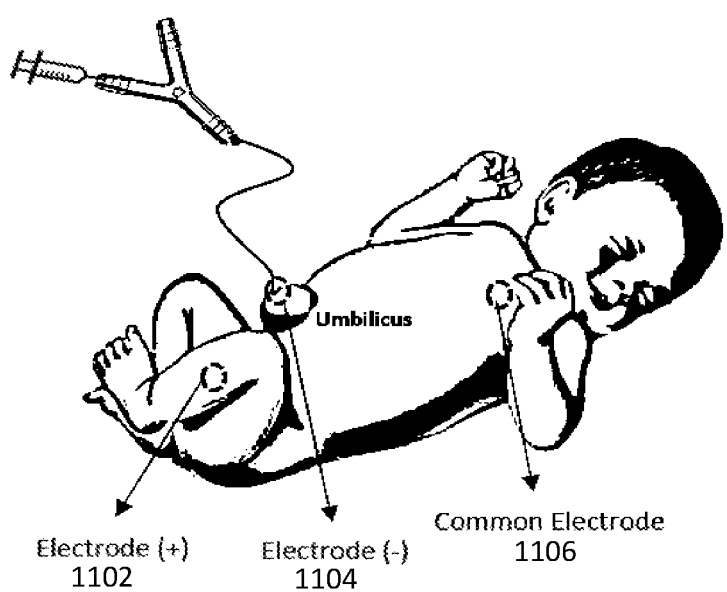
FIG. 11 is an illustration of an example placement of leads on a paediatric patient for recording a live ECG signal according to some embodiments of the disclosure.

Detecting catheter location in newborns is particularly challenging, due to the significant anatomical changes that occur in the first 28 days of life. In one example, a method may include receiving an intravascular electrocardiogram (ECG) signal from a tip of a catheter inserted in a paediatric patient, in this example a neonate, and receiving a surface ECG by placing standard ECG electrode pads on the skin of the patient. Some examples of ECG lead placement are shown in FIGS. 10 and 11, where at least one common electrode 1006, 1106 is placed on the patient. Optional surface ECG signals can be received via one or more surface electrodes 1002, 1009, 1102, with FIG. 10 showing a configuration for receiving a lead II surface ECG signal and FIG. 11 showing a setup for a unipolar intravascular ECG signal. The intravascular ECG signal is received using the catheter electrode 1104. The catheter electrode may be a saline column through the catheter, as is explained in further detail later. The ECG signal may be recorded, such as by buffering the ECG signal. The buffered signal may be processed in a signal processor to determine R-wave peaks and P-wave peaks in the surface ECG signal, and intravascular ECG signal. From an electrophysiology perspective, the intravascular ECG signal may also be considered in terms of A-wave and V-wave peaks in the intravascular ECG signal. Then, a location of the catheter in the neonate may be determined based on general and neonate-specific ECG characteristics (including artefacts) and under consideration of physiology and vascular anatomy of the neonate including extremity vessels, umbilical (cord) vein and umbilical (cord) artery identifying the catheter path at critical landmarks unique for neonatal anatomy where misplacement can occur, and, at least in part, on the P-wave peaks, R-wave peaks, (or A-wave peaks and V-wave peaks) using a trained machine-learning algorithm. The analysis for location determination is based on the surface and intravascular ECG signal, an electrical signal originating in the heart with voltage changes including those referred to as P-, Q-, R-, S-, A-, V- and H-waves. The neonatal ECG signal has features distinctly different from ECG signals from older patients. These ECG signal characteristics may be used advantageously to compare a recorded ECG signal to a trained model for neonatal ECG signals that correlates these characteristics to determine the catheter location.

In some embodiments, determining a location of the catheter may include determining a first average intensity of R-wave peaks in the buffered ECG signal and determining a second average intensity of P-wave peaks in the buffered ECG signal, and determining the location from the first average and the second average. In some embodiment, these averages may be normalized to a baseline ECG signal by receiving a baseline ECG signal from the skin surface of the patient. The surface signal is extremely useful for normalization mainly because any change in the anatomy and the cardiac axis angle is directly reflected in both the intravascular and surface ECG and a ratio between these signals is expected to result in an approximately constant output across different ages and different patients. Moreover, despite variations in the cardiac axis, the angle of the electrical vector formed by a lead II ECG is expected to give non-zero R-wave intensity thus avoiding infinite answers. In case of zones where the P-wave peaks might be zero or close to zero, the method will rely just on the normalized R-wave peak change. In another embodiment, the normalization step involves dividing the average intensity of P-wave peaks with R-wave peaks. A ratio between these two quantities is expected to be consistent despite anatomical variations as both factors directly reflect such changes. In case of zones with zero P-wave intensity, the algorithm will rely just on R-wave and proceed without normalisation till a non-zero P-wave peak is encountered.

It should be appreciated that the following method of ECG wave peak detection is described for the application of lead II surface ECG signals, however, this method may also apply to the analysis of intravascular ECG signals, i.e. A-wave, and V-wave peak detection.

A system for determining a catheter location is shown in FIG. 1. FIG. 1 is a block diagram illustrating a system for providing a catheter tip location to a user based on an electrical signal obtained from the catheter according to some embodiments of the disclosure. A catheter adapter 102 provides an electrical interface to a catheter being inserted in a neonate. The catheter adapter relays an electrical signal, containing the ECG signal, from the catheter to a signal processing unit (SPU) 104. The SPU 104 performs signal processing on the electrical signal to determine a location of the catheter. The SPU 104 may be a personal computer (PC), cloud-based server, mobile phone, tablet computer, embedded controller, or another device capable of being configured to perform signal analysis. The location information is passed as a signal to the user interface 106, which provides a display of the catheter location information to a user. The user interface 106 may display the location as a dot on a picture of a paediatric patient. The user interface 106 may display the surface and/or intravascular ECG waveforms. The user interface 106 may display one of several colours or shapes indicating whether the catheter is in a correct final location, whether the catheter is in an incorrect final location, whether the catheter is neither in a correct nor incorrect final location, or whether the catheter is advancing towards the correct or incorrect final location. The user interface 106 may include a liquid crystal display (LCD), a plurality of light emitting diodes (LEDs), a software window displayed on a mobile device separate to the SPU, or a software window displayed on the mobile device containing the SPU 104.

Figure 2:
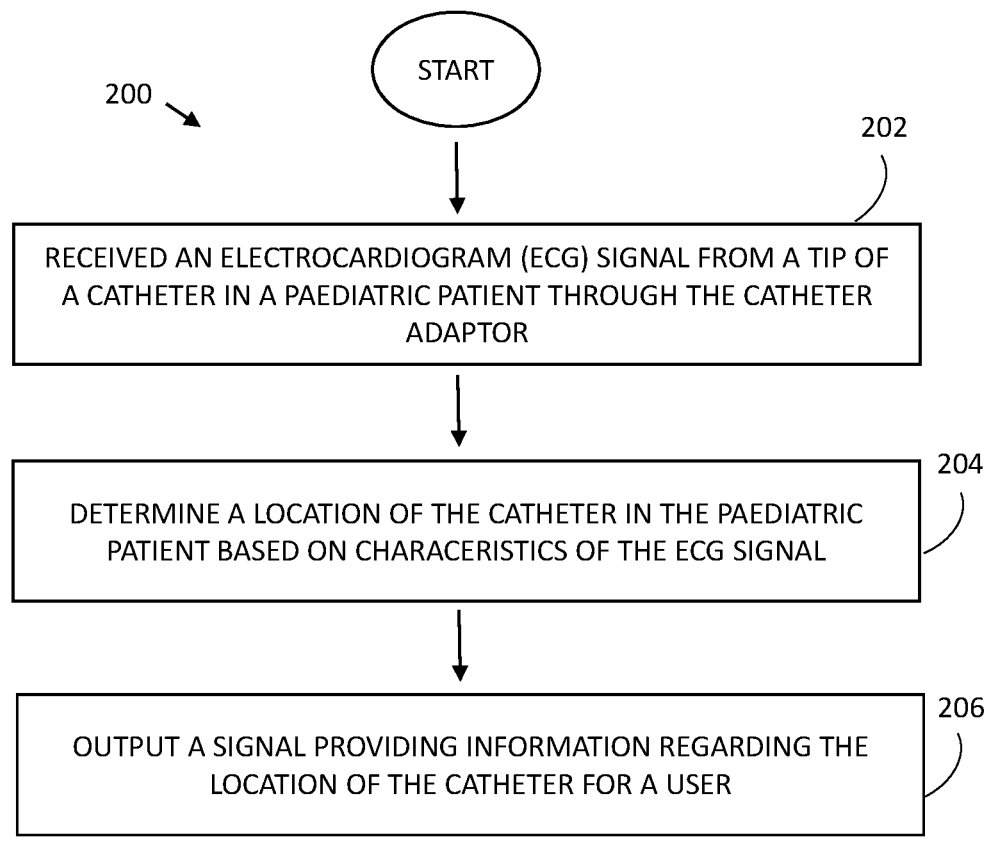
FIG. 2 is a flow chart illustrating an example method of providing a catheter location to a user based on an electrical signal obtained from the catheter according to some embodiments of the disclosure.

A method for signal processing with the SPU 104 is illustrated in FIG. 2. FIG. 2 is a flow chart illustrating an example method of providing a catheter location to a user based on an electrical signal obtained from the catheter according to some embodiments of the disclosure. A method 200 begins at block 202 with receiving an intravascular electrocardiogram (ECG) signal from the tip of a catheter inserted in a patient. A catheter adapter may be used to assist in interfacing the signal processor to the catheter. Optionally a surface ECG signal is also received. In some embodiments the surface ECG signal is used for normalisation of the intravascular ECG signal. In some embodiments the surface ECG signal can also be used during analysis of the intravascular ECG signal, for example to improve peak detection reliability. At 202 samples of the acquired ECG signals are also analysed to extract various useful characterising features from the intravascular ECG signals, for example P-wave peak amplitude, R-wave peak amplitudes, timing or location of the R and P wave peaks within each heartbeat recorded in the ECG signal, PR interval, QRS complex duration, heart rate etc. The features extracted may vary between embodiments and feature extraction is described in further detail below. This feature extraction may include normalisation of the extracted features, in some embodiments normalisation is performed based on features of the intravascular ECG alone and in other embodiments baseline signals received from a surface ECG are utilised for normalisation, some embodiments can use a combination, and all such options are contemplated. The feature extraction and normalisation options are described in further detail below.

Next, at block 204, a location of the catheter in the neonate is determined based on characteristics of the ECG signal recorded and extracted as features at block 202. The determination is performed by inputting the extracted features to one or more trained machine learning algorithms, trained to predict the location of the catheter tip (described in further detail below). Then, at block 206, a signal is output that provides the location information, which may be output to a user through visual feedback, audio feedback, tactile feedback, or other feedback mechanisms, for example outputting data to a remote monitoring/notification system for the hospital or outputting data to a file for storing to patient records. The signal processing of FIG. 2 may be used during catheter insertion and while the catheter remains in place.

The various embodiments of the invention utilise different combinations of feature extraction and analysis techniques. Various embodiments are explained in the examples below. However, it should be understood that any combination of the methods described in detail may be used.

Figure 3A:
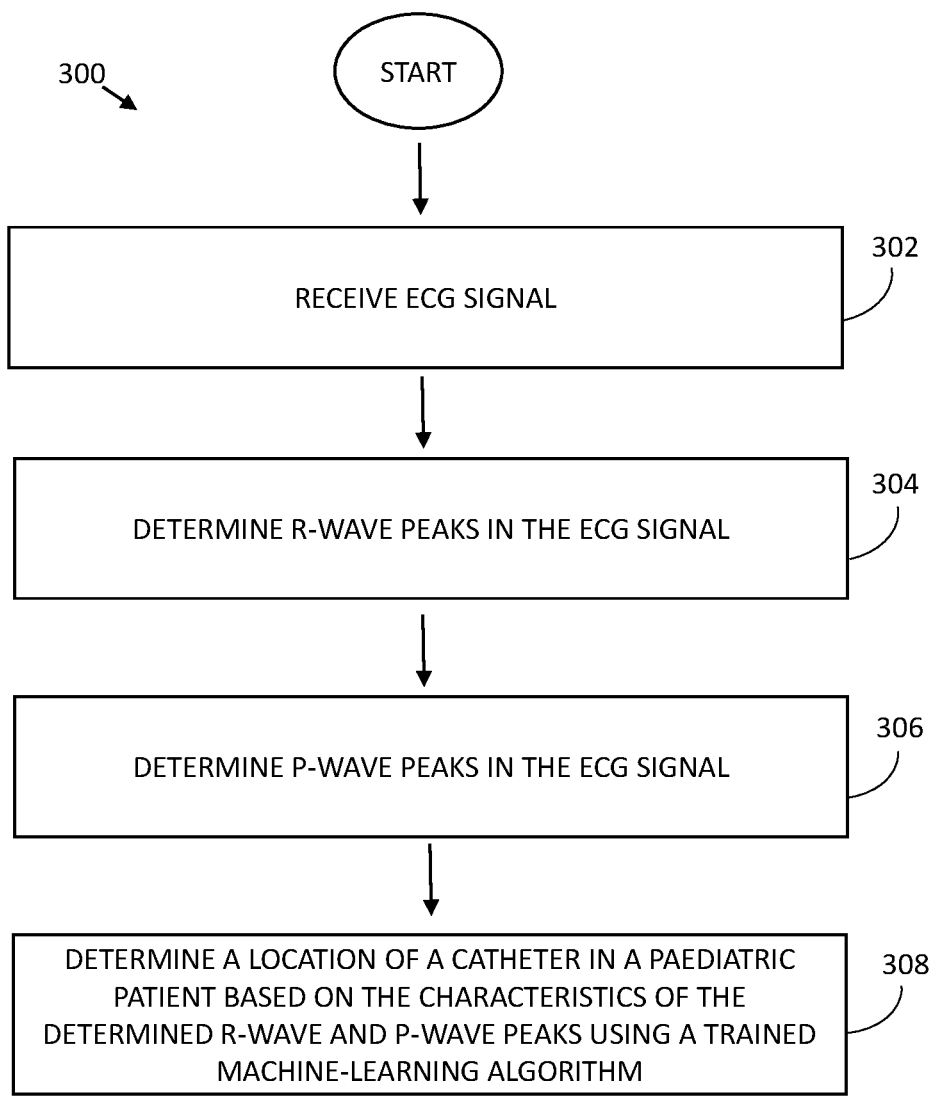
FIG. 3a is a flow chart illustrating an example method of determining catheter location based on R-wave and P-wave peaks in an ECG signal according to some embodiments of the disclosure.
Figure 3B:
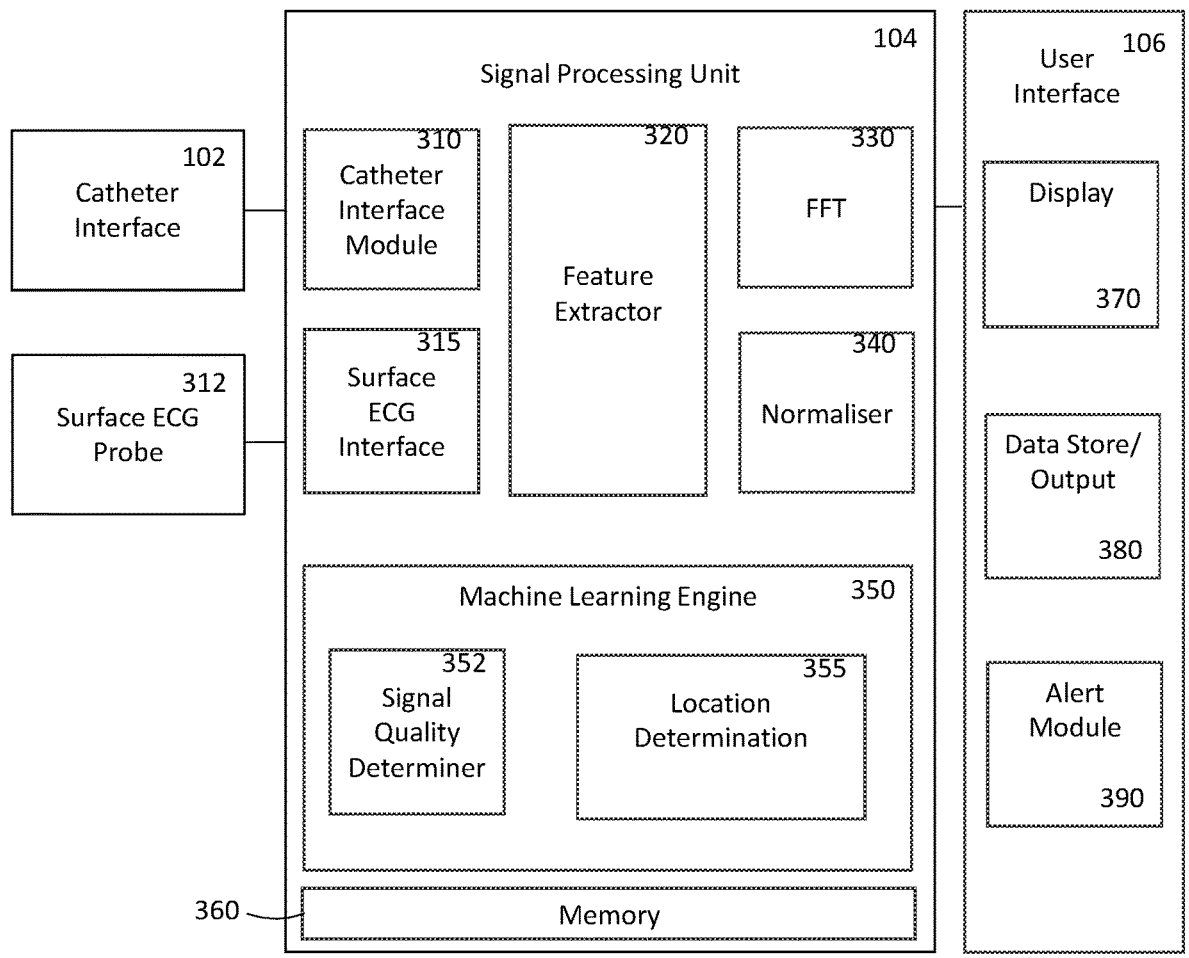
FIG. 3b is a block diagram illustrating a system for providing a catheter location to a user based on an electrical signal obtained from the catheter according to some embodiments of the disclosure.

One embodiment for determining catheter location using the ECG signal is based on the location of R-wave and P-wave peaks in the intravascular ECG signal and optionally surface ECG signals. R-wave and P-wave peaks may be chosen because these peaks are found to be consistent among different patients, including neonates. FIG. 3a is a flow chart illustrating an example method of determining catheter location based on R-wave and P-wave peaks in an ECG signal according to some embodiments of the disclosure. FIG. 3b is a block diagram of an embodiment of a system which may be used to implement various method embodiments. The system comprises a catheter interface 102, signal processing unit 104 and user interface 106. The signal processing unit 104 includes processing resources and memory 360 for buffering and storing of ECG signals and extracted feature data. The SPU 104 of this embodiment implements a catheter interface module 310, and optional surface ECG interface module 315, a feature extractor 320, machine learning engine 350, an optional FFT module 330, and optional normalisation module 340. It should be appreciated that these functional modules may be implemented in software running on dedicated SPU hardware, such as a server, tablet or PC, alternatively the SPU may be implemented using one or more devices and/or distributed processing resources configured through software to operate as a system. In alternative embodiments dedicated hardware may be used, for example feature extraction may be implemented using a hardware solution to improve processing speed, for example programmable hardware such as a field programmable gate array (FPGA) or fixed application specific integrated circuit (ASIC).

A method 300 begins at block 302 with receiving an ECG signal via a catheter interface 102 by a catheter interface module 310. At blocks 304 and 306, R-wave peaks and P-wave peaks are determined, respectively, from the received ECG signal by the feature extraction module 320. At block 308, the location is determined by the machine learning engine 350 based on characteristics of the determined R-wave and P-wave peaks, in particular the relative location and amplitude of the R-wave peak and P-wave peak within the intravascular ECG signals. The R-wave and P-wave peak characteristics may be input to a trained machine-learning engine 350, and the location determination module 355 of the engine outputs a location based on the R-peak and P-peak locations and R-peak and P-peak amplitudes of the peaks in the ECG signal. The peak detection algorithms label the indices or the specific samples or time points in the waveforms as the peak locations. The values of the waveform at these locations are tagged as the peak amplitude. They can also be referred to as peak voltages or peak height and they are relative to the corresponding peak amplitudes/height/voltages in the surface signal. The machine-learning engine implements at least one machine learning algorithm and may establish a model for determining catheter location by training the algorithm with labelled clinical data. The machine-learning engine may include one or more of an artificial neural network algorithm, a deep learning algorithm, a Bayesian network algorithm, a decision tree learning algorithm, and a rule-based learning algorithm. Other numerical methods may also or alternatively be used to determine the location using the peak locations from the ECG signal. In some embodiments, the location may be determined by transmitting the peak information to a cloud-based server hosting a machine-learning algorithm and receiving the location from the cloud-based server. In some embodiments, the method 300 may also include determining other measurements and calculations used to adjust for general and neonate specific ECG characteristics and artefact correction.

The machine learning engine includes location determination module to perform location analysis. Location involves training and implementation of machine learning derived models which use the pre-processed ECG features to predict the catheter location based on data classification or regression. The training scheme for each step requires a set of pre-recorded intravascular ECG tracings. These datasets are used to train and test a learning system and derive specialized mathematical models through it.

Figure 4:
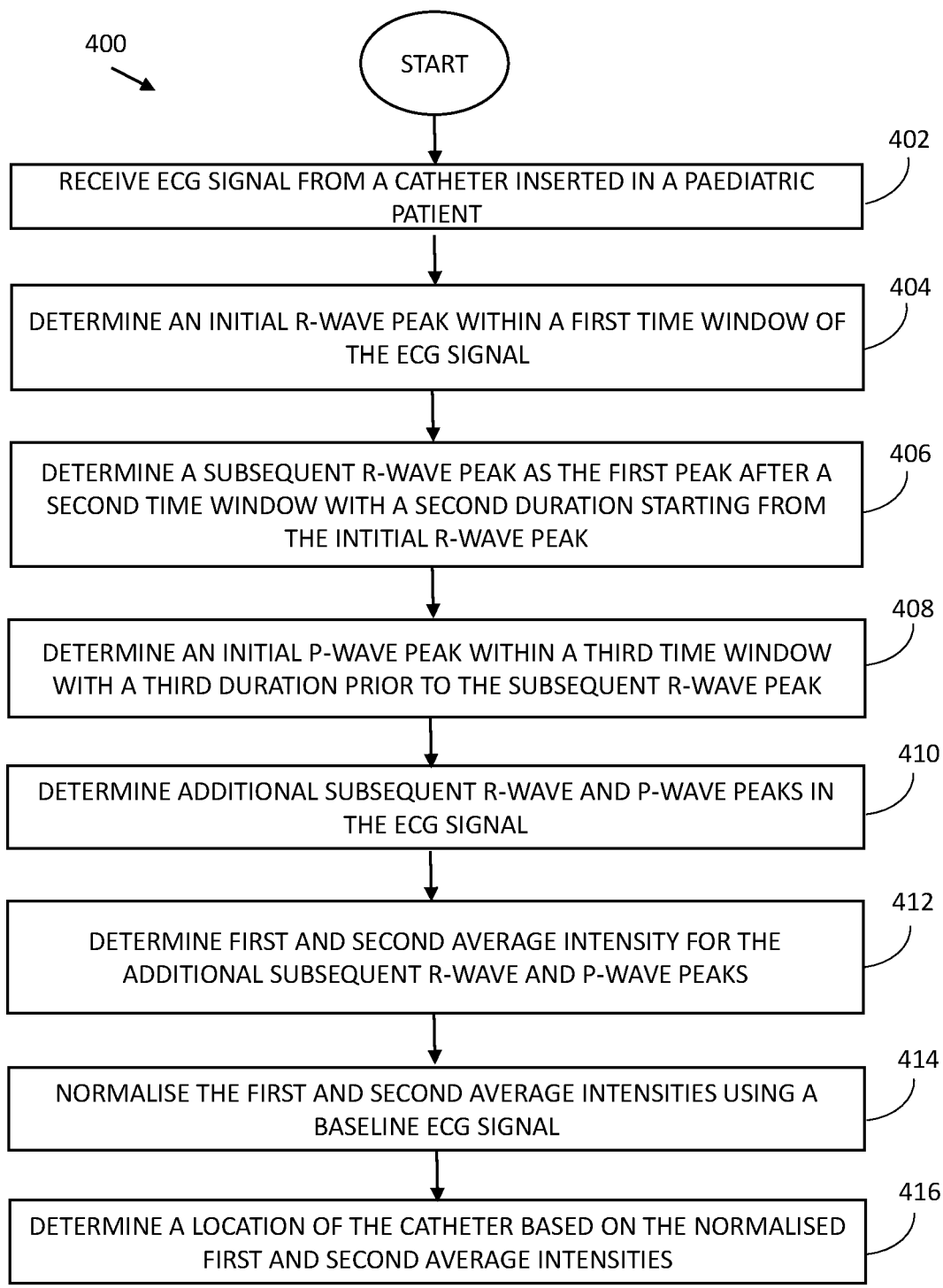
FIG. 4 is a flow chart illustrating an example method of determining catheter location with R-wave and P-wave peaks normalized using a baseline ECG signal according to some embodiments of the disclosure.

One algorithm for determining characteristics of the ECG signal to ultimately determine the catheter location is illustrated in FIG. 4. FIG. 4 is a flow chart illustrating an example method of determining catheter location with R-wave and P-wave peaks normalized using a baseline ECG signal obtained from a surface ECG probe according to some embodiments of the disclosure. For the baseline ECG, prior to the start of the procedure, a surface lead II ECG is captured during a small time window to use as the baseline for data normalisation. The catheter location method 400 for a neonate illustrated in FIG. 4 begins after the baseline ECG capture at block 402 with receiving an ECG signal from a catheter inserted in a neonate. R-wave and P-wave peaks are determined in the ECG signal in blocks 404, 406, 408, 410, and 412. This embodiment of the method 400 makes use of characteristics of neonatal ECG signals: that the newborn heart-rate is normally higher than that of an adult and sits in the range of 146 to 160 beats per minute (bpm) and does not vary much during the catheterization procedure, that the R-wave peak stays maximum among other ECG features at all commonly encountered locations (except when the catheter is too deep in the Right Atrium) during CVC procedures, that the average heart rate is consistent across neonates at approximately 146 beats per minute (bpm) and does not vary much during the catheterization procedure, that the PR-interval from a start of the P-wave until the beginning of the QRS-complex, averages at 100 milliseconds (with very small variations) for neonates aged 0-30 days old, and that the QRS duration from a start of the QRS-complex to an end of the QRS-complex averages at 50 milliseconds (with very small variations).

Figure 5:
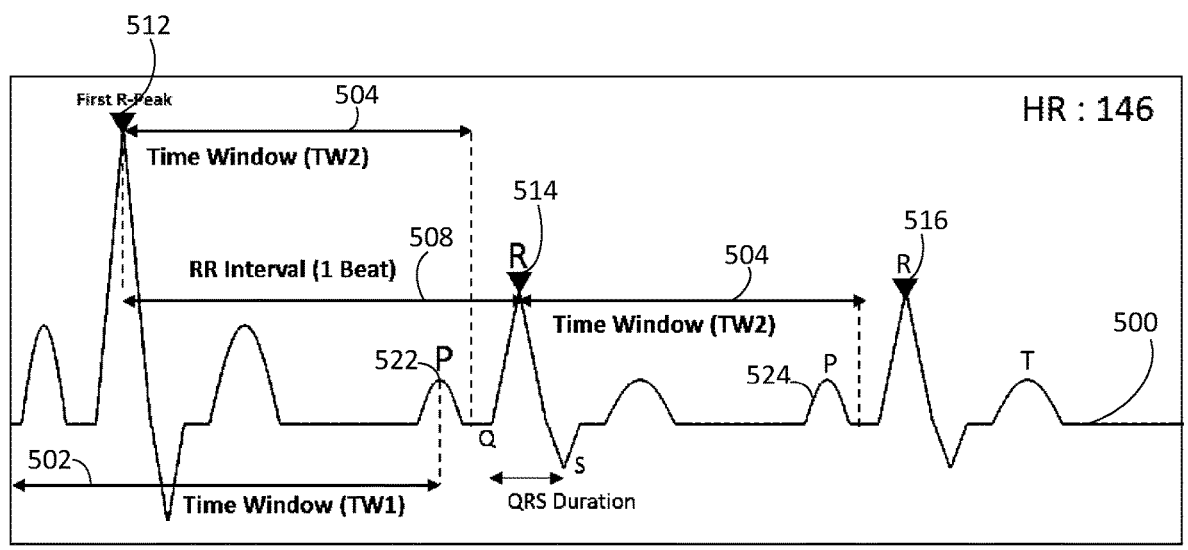
FIG. 5 is a graph illustrating an example determination of R-wave and P-wave peaks using an algorithm according to some embodiments of the disclosure.

R-wave peaks are determined at blocks 404, 406, and 412. The determination of R-wave peaks begins with defining a first time window (TW1) having a first duration approximately equal to the time required for one full heartbeat to occur at a neonatal heart rate of 146 bpm. This first time window can have a predetermined duration, set or selected by an operator prior to the procedure (for example based on patient age or medical record data) or may be determined by the system, for example based on standard hear rate detection using the surface ECG signal. The first time window is applied to a live ECG signal, such as the ECG signal being buffered in memory 360 as it is received at block 302 from the catheter via the catheter interface module 310. At block 404, an initial R-wave peak is identified as the highest amplitude peak in the first time window of the ECG signal. The method 400 is applied for peak determination in a sample ECG signal shown in FIG. 5. FIG. 5 is a graph illustrating an example determination of R-wave and P-wave peaks using an algorithm according to some embodiments of the disclosure. A first time window TW1 502 is applied to ECG signal 500. The time window duration TW1 is chosen to be approximately the duration of one heart-beat, based on the average heart rate for the patient and can be based on an age range, for example 146 BPM for a neonate. The signal analysis can start from an arbitrary position within the heart beat cycle of the monitored ECG signal. For example, analysis may start from a point in the ECG signal trace where the first peak in the time window is that of a T-wave or P-wave or an R-wave. Having a time window that is equivalent to at least one heartbeat (RR interval) can ensure that the first time window will always encounter an R-wave. The largest peak in the window 502 is peak 512, which is determined to be a R-peak. At block 406, a subsequent R-wave peak is identified using a second time window (TW2). The first time window TW1 may be used only for detection of the first R wave in a sample. Optionally, the RR-interval, determined from the subsequent peak detection described below may be used to set the duration of the first time window TW1 for analysis of subsequent samples.

The second time window TW2 504 is defined as starting at the R-wave peak 512 and having a duration approximately equal to the RR-interval less half of the QRS duration. The duration of TW2 is calculated based on known characteristics of the neonate heartbeat as described above, such that the time window TW2 should be shorter than the RR interval 508 or heartbeat duration. The duration of time window TW2 may be derived from the duration of the first time window TW1. The time window TW2 will typically be marginally shorter than the first time window TW1, for example shorter by a portion of the QRS complex duration. Where TW1 is equal to the RR interval, then TW2 will be shorter than TW1 by half the QRS duration, to avoid occurrence of two R peaks within the second window TW2. The time window TW2 may be adjusted in accordance with the specific heart beat characteristics for the patient, if necessary. The next peak in the ECG signal 500 after the TW2 window 504, which is peak 514, is the subsequent R-peak. Additional subsequent R-peaks can be identified at block 410 using a similar technique of applying the second time window TW2 to a determined R-peak, and determining the next peak after the time window TW2 to be the next R-peak. A factor of safety can be used to modify the time windows 502 and 504 to account for unexpected events in the ECG signal. For example, the neonate heart rate used to determine the duration of the time windows 502 and 504 may be updated in real-time during the insertion of the catheter based on determined R-peaks. For example, the neonate heart rate may be calculated using five seconds of buffered ECG signal as the number of R-peaks determined in the past five seconds multiplied by 60 and divided by 5.

Figure 6:
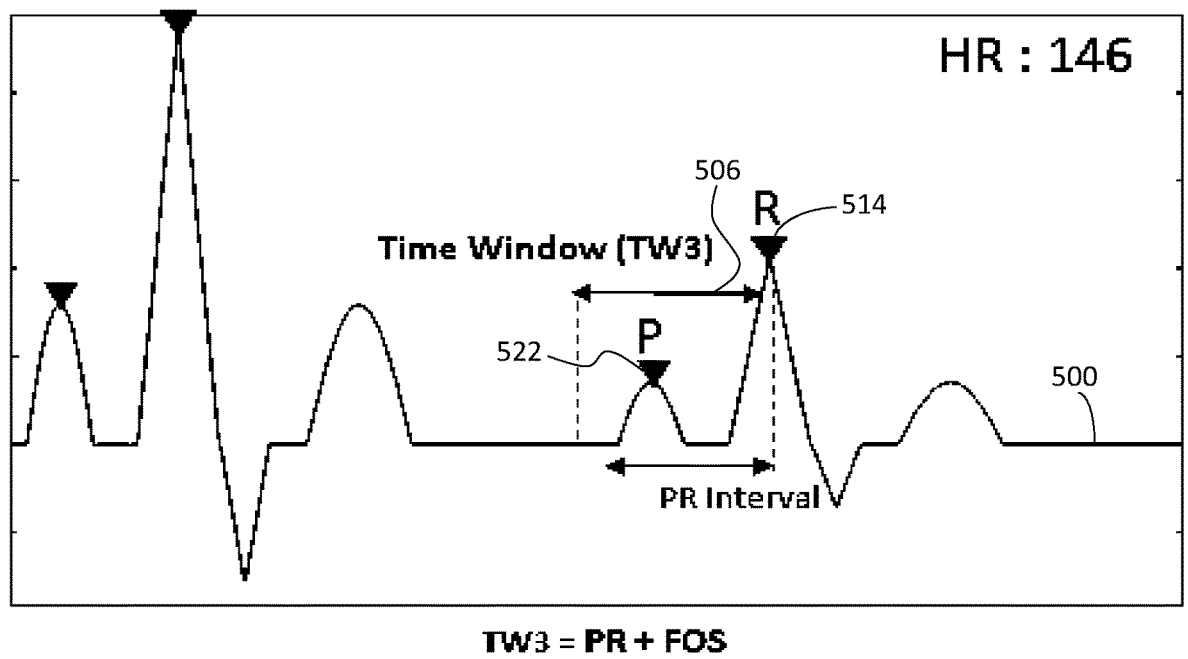
FIG. 6 is another graph illustrating an example determination of R-wave and P-wave peaks using an algorithm according to some embodiments of the disclosure.

P-wave peaks may be determined at blocks 408 and 410 based on the determined location of R-wave peaks. Here the location refers to the specific sample or time point in the measured signal where the R-wave peak occurs. The idea is to draw a window along the temporal axis to the left of this location (where the R-wave peak lies) and use that to determine the P-wave location and the peak amplitude. At block 408, an initial P-wave peak is determined by defining a third time window with a third duration prior to the subsequent R-wave peak of block 406. An example P-wave peak determination is shown on a sample ECG signal in FIG. 6. FIG. 6 is another graph illustrating an example determination of R-wave and P-wave peaks using an algorithm according to some embodiments of the disclosure. The peak 514 corresponds to a determined R-peak. A time window TW3 506 prior to the peak 514 is identified with an approximate duration of the PR-interval, and optionally a factor of safety (FOS). The FOS is chosen to stretch the time window, to capture slightly more of the ECG signal, to make sure any immediate changes to the heart rate are accounted for. The duration of the window TW3 506 can be calculated based on known characteristics of the PR interval for neonates and adding a safety factor. The maximum value in window 506 is determined as the P-wave peak, shown as peak 522. At block 410, additional subsequent P-wave peaks are identified from determined R-wave peaks in a similar manner to identify P-wave peaks 524. It should be appreciated that in this embodiment when used for neonates, feature extraction is simplified by using a methodology based on peak detection within a window, where the window durations are calculated based on known ECG signal characteristics for neonates.

After R-wave and P-wave peaks are identified in an ECG signal at blocks 404, 406, 408, and 410, characteristics of the ECG signal are determined from the identified peaks at block 412. An example characteristic is an amplitude of the R-wave and P-wave peaks in the RR-interval 508 of the ECG signal 500, the amplitude of several peaks in adjacent RR-intervals can be measured and averaged. A first average corresponding to the average amplitude of the R-wave peak may be determined at block 412. A second average corresponding to the average amplitude of the P-wave peak may also be determined at block 412. The average may correspond to a recent portion of the ECG signal, such as the previous five seconds of ECG data buffered in memory from the catheter. Averaging these extracted features enables each feature to be characterised by a single value for the time period for input to location determination. These averages may optionally be normalized by a baseline ECG recording for the neonate receiving the catheter at block 414.

The location of the catheter may be determined at block 416 from the normalized first and second averages. In this embodiment the catheter location can be determined by the machine learning engine 350 location determination module 355 based on a ratio between the averaged intravascular P-wave peak amplitude and averaged intravascular R-wave peak amplitude. It should be appreciated that this embodiment does not require use of a surface ECG signal, as the ratio of the averaged intensities of the R-wave peaks and P-wave peaks is expected to be consistent despite anatomical variations between patients—as both the R and P wave peaks reflect the same anatomical variations. In this embodiment, averaging the extracted features and using ratios has a normalising effect.

Figure 17A:
FIGS. 17a and 17b show ECG signals for neonates at different stages of development (age) to provide an example illustrating how the ECG signals can change with age.
Figure 17B:
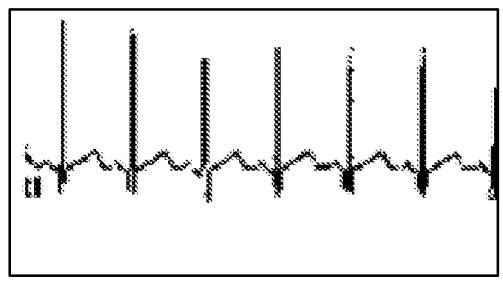
Figure 18A:
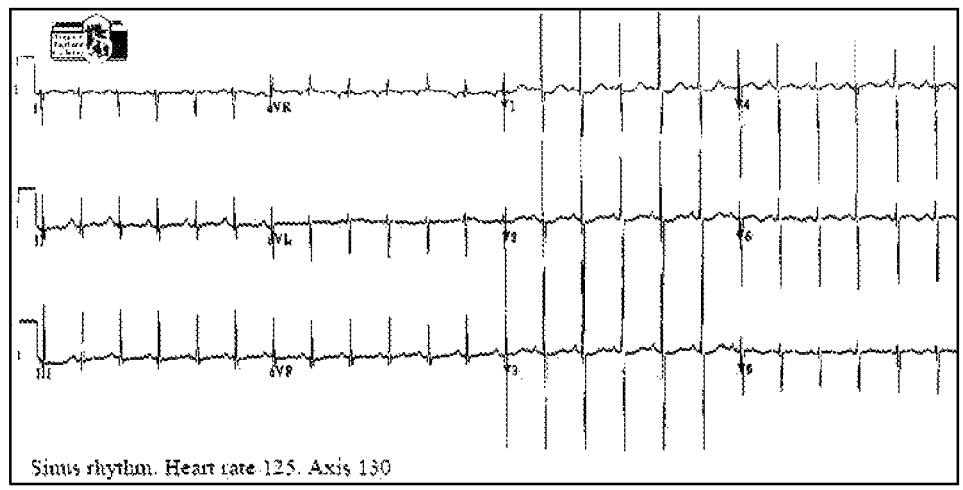
FIGS. 18a, 18b and 18c show surface lead ECG signals for a one day old infant, a 2 day old infant and a 3 week old infant respectively.
Figure 18B:
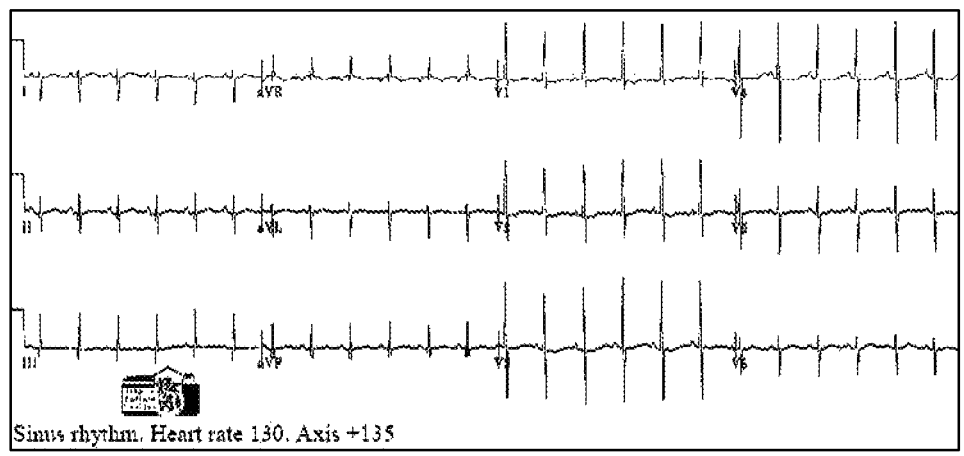
Figure 18C:
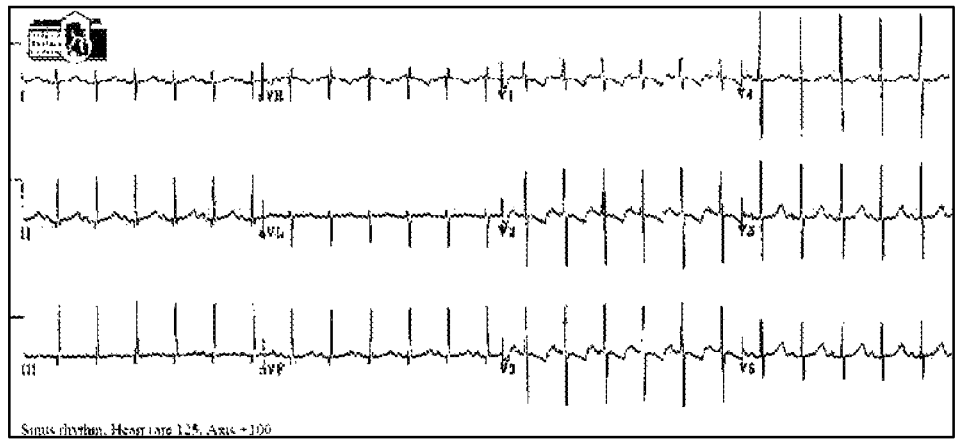

Data normalisation can be performed on the extracted features to make the input to the location analysis model consistent across different patients and ages. Particularly for different neonatal ages where interpatient variation can be significant. In the first few weeks of birth, a neonate's cardiovascular system undergoes significant changes—important parts of the system like Ductus Arteriosus, Ductus Venosus and Foramen Ovule change their physical state as the body is no longer receiving circulation from the mother. These age-related changes directly affect the electrical activity of the heart and the fact they may occur at different rates in different patients poses a significant challenge towards the catheter-location analysis. Some of these anatomical changes are reflected through a varying cardiac axis with respect to which an ECG recording is made. A change in the cardiac axis angle can lead to a different P-wave and R-wave shape or amplitude which are the vital features in the location analysis. The cardiac axis of 0 to 1-days old newborns varies from 59 to 192 degrees while for infants aged 1-3 months it goes down to 31 to 114 degrees, an example of two different neonate ECG signals is shown in as shown in FIGS. 17a and 17b, where FIG. 17a shows an ECG of a one day old baby with a cardiac axis of 130 degrees compared with FIG. 17b which shows an ECG of a two month old infant with cardiac axis at 80 degrees. FIGS. 18a-c show further examples of neonate ECG signals, with FIG. 18a showing examples of ECG signals taken from limb leads (Lead I, II, III) for a 1 day old infant ECG signals, FIG. 18b shows examples of similarly measured ECG signals for a 2 day old infant, and FIG. 18c shows examples of similarly measured ECG signals for a 3 week old infant. From these images it should be appreciated how rapidly neonate heartbeats change with age. Table 1 also shows changes in frontal plane (limb leads) QRS Axis with respect to a newborn's age.

TABLE 1

Normal neonatal ECG standards

| AGE GROUP | HEART RATE (BEATS PER MINUTE) | FRONTAL PLANE QRS AXIS (DEGREES) $2^{ND}$-$98^{TH}$ PERCENTILE (MEAN) |
|---|---|---|
| 0-1 days | 93-154 (123) | +59 to +192 (135) |
| 1-3 days | 91-159 (123) | +64 to +197 (134) |
| 3-7 days | 90-166 (129) | +77 to +187 (132) |
| 7-30 days | 107-182 (149) | +65 to +160 (110) |
| 1-3 months | 121-179 (150) | +31 to +114 (75) |

It should be noted that the terms QRS axis and cardiac axis are used interchangeably. The population-based variations can affect the placement of the catheters, for example, where for instance a liver intravascular signal for one neonate might differ significantly from another. On the other hand, the age-related variations can directly impact the catheter migration analysis where the signals at the same anatomical location at one point in time might change significantly at a later point in time. A general solution is required to take care of these volatile changes. Two methods based on two different normalisation factors for data normalisation are discussed. The above example uses intravascular signal feature averaging and use of ratios.

In an alternative example a surface ECG signal can be used for normalisation. In this second method, a surface (lead II) ECG is captured prior to the procedure and is subjected to the feature extraction algorithm to acquire P-wave and R-wave peaks—referred to as baseline P-wave and R-wave peaks. These baseline P-wave and R-wave peaks amplitudes (intensities) are averaged across a short time window (for example 5 seconds). A ratio of the averaged surface (baseline) ECG P-wave peak amplitude and averaged intravascular P-wave peaks amplitudes provides the normalised P-wave peak amplitude value. Similarly, a ratio of the averaged surface ECG R-wave peaks amplitude and averaged intravascular R-wave peaks amplitude provides the normalised R.-wave peak amplitude value. These normalised values can then be used for catheter tip location determination. The surface ECG signal is extremely useful for normalisation, mainly because any change in the anatomy and the cardiac axis angle is directly reflected in both the intravascular and surface ECG and a ratio between these signals is expected to result in an approximately constant output across different ages and different patients (for example, neonates, infants, toddlers, children and adolescents). Normalisation can compensate for patient based variation and therefore enable more consistent (less individual patient variation) signal to be input to the catheter tip location analysis by the machine learning engine. Moreover, despite variations in the cardiac axis, the angle of the electrical vector formed by a lead II ECG is expected to give non-zero R-wave peaks thus avoiding infinite answers. In case of commonly encountered locations (for example Liver in UVC) where the P-wave peaks might be zero or close to zero, the method for determining catheter tip location can rely on just the R-wave peak change, and can proceed without normalisation till a non-zero P-wave peak is encountered.

Other methods may be used to determine the location of R-wave and P-wave peaks. For example, the known Pan and Thompkins method may be used for R-wave peaks. Regardless of the method of determining the peaks, the average amplitude of those peaks in the ECG signal may be used to determine the location of the catheter.

Figure 7:
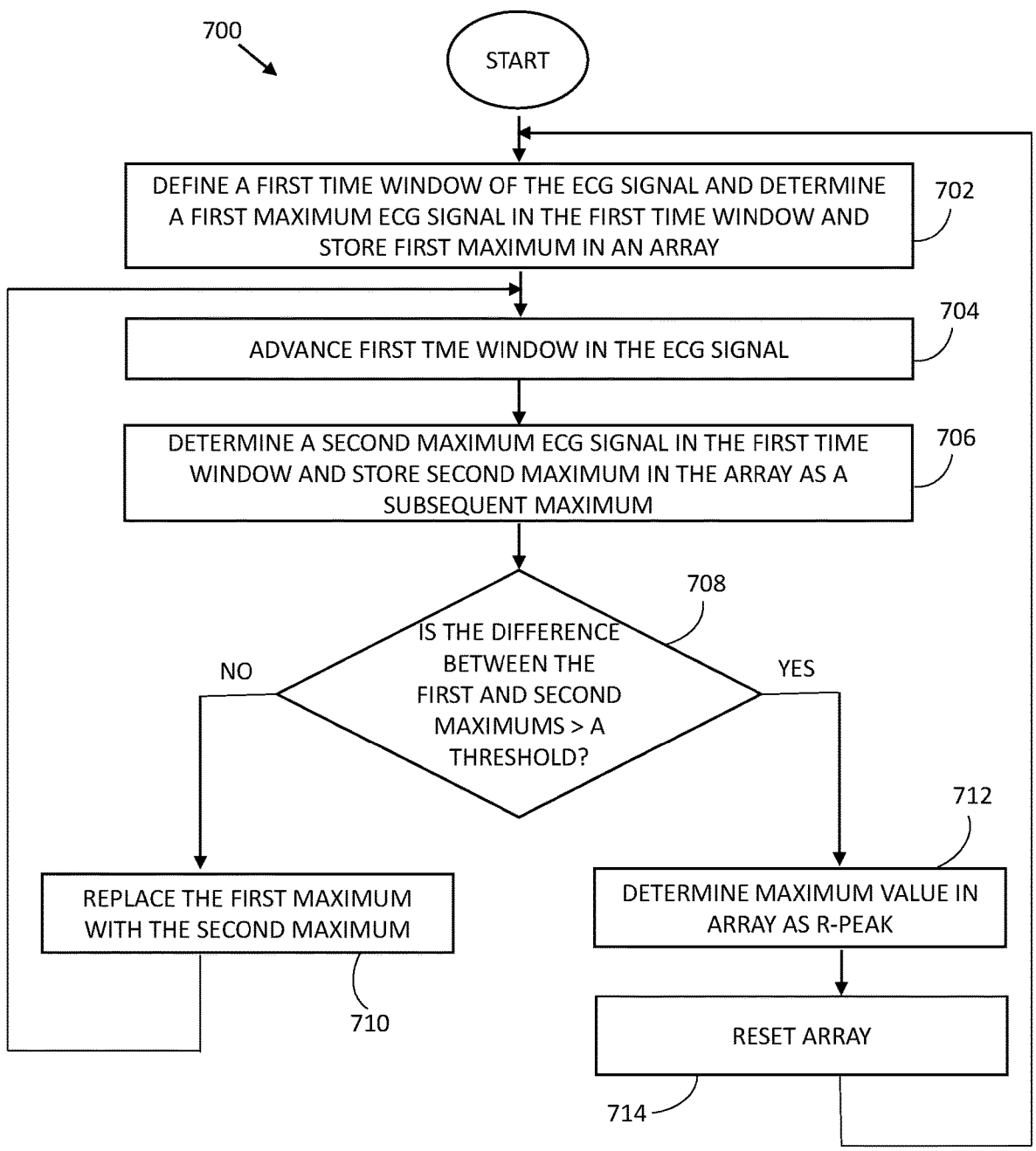
FIG. 7 is a flow chart illustrating an example method of determining R-wave and P-wave peaks using a sliding time window according to some embodiments of the disclosure.
Figure 8:
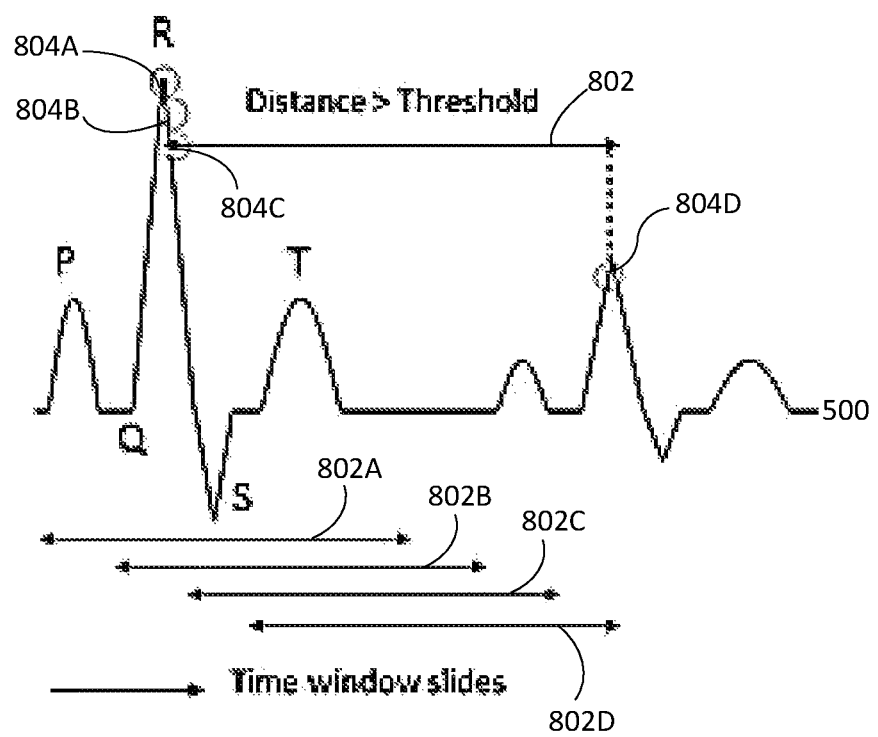
FIG. 8 is a graph illustrating an example determination of R-wave peaks using a sliding time window according to some embodiments of the disclosure.

Another example method of identifying R-wave and P-wave peaks is illustrated in FIG. 7. FIG. 7 is a flow chart illustrating an example method of determining R-wave and P-wave peaks using a sliding time window according to some embodiments of the disclosure. A method 700 begins at block 702 with defining a first time window of the ECG signal and determining a first maximum ECG signal in that first time window. The duration of the first time window may be selected using the normal upper limit of a patient (for example, neonate, or based on age ranges) heart rate, which allows the time window to be practical as well as sufficiently small so that it is unlikely that two consecutive R-peaks will appearing in the same window. The time window duration may also be adjusted once consecutive R peaks are identified, if necessary. The duration is also reasonably long enough to allow a subsequent R-peak to appear in the time window as soon as the time window passes the first R-peak. The duration of the time window may be preselected or determined from the ECG signal (either the intravascular ECG or a surface ECG) using conventional methods. The maximum value is stored in an initially-empty array. An example of the determination is shown on a sample ECG signal in FIG. 8. FIG. 8 is a graph illustrating an example determination of R-wave peaks using a sliding time window according to some embodiments of the disclosure. A time window 802A applied to the ECG signal 500 identifies a maximum value 804A. At block 704, the time window is then advanced in the ECG signal to window 802B. A maximum value 804B in the ECG signal 500 is determined for the time window 802B and stored in the array as a subsequent (second) maximum value. The difference between the previous two maximum values is compared to threshold criteria at block 708, the threshold criteria include a threshold temporal difference between the maximum values determined for each window. If the difference is less than the threshold, then the processor feature extraction module assesses the maximum value as relating to the same peak as the maximum within the first window. The method 700 continues through block 710 to store the second maximum as the first maximum and return back to block 704 to advance the window and to block 706 to determine a new second maximum. For example, the time window 802B advances to the time window 802C to identify maximum value 804C. The difference between values 804C and 804B is less than the threshold, thus the time window advances to time window 802D to identify maximum value 804D. The temporal difference between values 804D and 804C is greater than the threshold at block 708. The maximum of the maximum values 804A, 804B, 804C, and 804D is determined to be an R-peak 804A at block 712, and the array of maximum values is reset at block 714. Conceptually, this may be understood as the window stops moving as soon as the temporal distance between the previous maximum and the current maximum is greater than a threshold. In an embodiment the threshold may be defined as half of a normal RR-interval for the patient age range (for example, neonate, 3-6 months, 6-12 months, 1-2 years, etc.) and its purpose is to simply stop the moving window. In a system configured for use with neonates, the threshold can be set greater than the average neonatal PR and QT intervals so that even at lower heart rates, it avoids the sliding window to stop at maximum of P-wave or T-waves. This is especially helpful when the heart rate is smaller and the ECG wave for 1 beat is bigger in the temporal axis.

The method 700 then returns to block 702 to repeat the process and determine the location of the next R-wave peak. Progressing the window towards 804D such that 804D can be confirmed during the repetition of steps 704 to 712 as the next R-wave peak. As R-wave peaks are determined, P-wave peaks may be determined using a similar process as described above with reference to FIG. 6. The determined R-wave and P-wave peaks may be used to determine characteristics of the ECG signal 500 useful for determining the location of the catheter. For example, the characteristics of the ECG signals can include selections of R-wave peak amplitude, P-wave peak amplitude, R-wave peak location (timing), P-wave peak location (timing), PR interval, RR interval etc.

Due to unforeseen variations in the ECG signal, identification of R-wave peaks through the aforementioned methods may lead to false positives where an actual T-wave or P-wave peak might be classified as an R-wave peak. Correction checks can be done prior to P-wave peak detection to remove/change the misclassified peaks. Misclassified P-wave peaks can be corrected by evaluating detected R-wave peaks that span within a time window equivalent to the sum of PR interval and a factor of safety. All detected pairs will have the first occurring peak removed and peak after the first tagged as R-wave peak since physiologically in a specific beat, P-wave peaks occur before the QRS complex. P-wave peaks may also be misclassified in instances where P-wave peaks are larger than R-wave peaks in which case, presence of a smaller undetected peak after every detected peak in the same time window as above is evaluated. If a peak is present and is smaller than the previous detected peak, then it will be tagged as the new R-wave peak. The time window constructed using the PR interval is small enough to prevent the T-wave peak being used in the correction check. Correction of misclassified T-wave peaks can be performed using a similar method as P-wave correction except here, the time window is constructed through the QT interval (average at 400 ms for a neonate) plus a factor of safety and the first occurring peak is tagged as R-wave peak while the peak after is removed. It should be noted that physiologically the QRS complex occurs before the T-wave.

Figure 19:
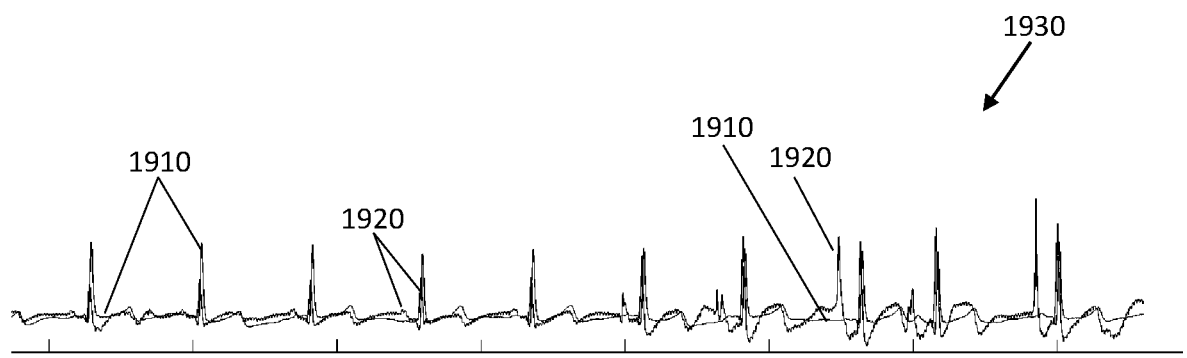
FIG. 19 shows an example of overlapping traces for a surface ECG signal and intravascular ECG signal.

In some embodiments, using any of the peak detection methods discussed above, peak detection accuracy can be improved by also applying the peak detection method to a real-time surface ECG captured at the same time as the intravascular ECG (IECG) throughout the procedure. The time locations of R-wave and P-wave peaks detected on the surface signal are expected to roughly coincide with the same features of the IECG. Detecting the R-wave and P-wave peaks in the surface ECG signal, enables cross checking with the peak detection outcomes for the IECG signal. An example of overlapping traces for a surface ECG 1910 and IECG 1920 are illustrated in FIG. 19, from this it can be observed how the surface ECG 1910 remains substantially regular and may be utilised as a reference for the timing of R and P wave peaks in the corresponding IECG 1920, particularly where the IECG shows significant variation in region 1930. This can ensure that the IECG signal peaks around these time locations are tagged as the corresponding P and R-wave peaks. The volatile nature of IECG sometimes may cause the previous peak detection algorithms to throw false positives. However, surface ECG signals being more stable (because of relatively less movement of the electrodes) can significantly improve the accuracy of the peak detection. Highly accurate peaks reduce the sensitivity of the peak detection algorithms to random artefacts in a signal train and can also be instrumental in determining both the absent peaks and very small peaks.

Figure 9:
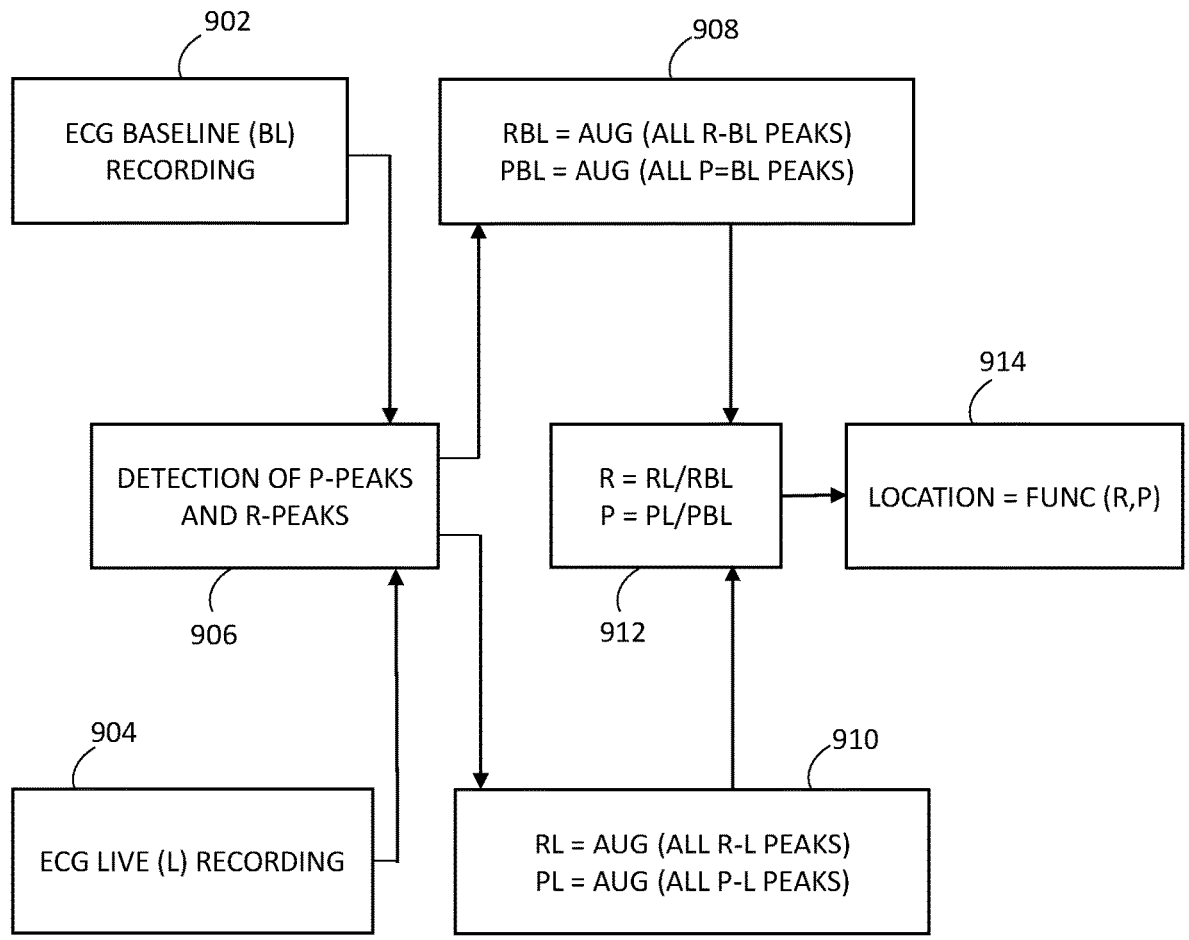
FIG. 9 is a block diagram illustrating an example method of determining catheter location based on normalized R-wave and P-wave peaks according to some embodiments of the disclosure.

An example computation of the catheter tip location based on R-wave and P-wave peaks that may be implemented in a signal processing unit (SPU) is shown in FIG. 9. FIG. 9 is a block diagram illustrating an example method of determining catheter location in UVC procedure based on normalized R-wave and P-wave peaks according to some embodiments of the disclosure. A baseline ECG recording (BL) is stored at block 902. A live ECG recording (L) for a is stored at block 904. At block 906, P-peaks and R-peaks are determined in the recorded baseline (BL) and live (L) ECG signals. Average intensities within the sample window for R-peaks (RBL) and P-peaks (PBL) for the baseline (BL) ECG signal are determined at block 908. Average intensities for R-peaks (RL) and P-peaks (PL) for the live (L) ECG signal are determined at block 910. A first value R, a normalized R-peak average amplitude, is determined as the ratio of RL to RBL at block 912. Also, at block 912, a second value P, a normalized P-peak average amplitude, is determined as the ratio of PL to PBL. At block 914, a catheter location is determined as a function of the R and P values. The function may be a trained machine-learning algorithm that determines a probability that the catheter is at a plurality of locations. For example, the function may return a probability that the catheter is in the liver, a probability that the catheter is in the spleen, a probability the catheter is in the IVC, a probability that the catheter has been advanced through the ductus venosus but is below the IVC, and/or the probability the catheter is in the atrium. In another example, the function may return an integer value corresponding to a location of highest probability, and that value used in a look-up table to determine the closest location. The function may return a '1' value for spleen, a '2' value for liver, a '3' value for IVC, a '4' value for below the IVC but past the ductus venosus, and/or a '5' value for atrium.

Some or all of the various processing in blocks 902, 904, 906, 908, 910, 912, and 914 may be performed by the signal processing unit (SPU). In one embodiment, the SPU is a personal computer. The ECG signal may be received through a Universal Serial Bus (USB) port and processed by the central processing unit (CPU) of the personal computer according to blocks 902, 904, 906, 908, 910, 912, and 914. In another embodiment the SPU is a mobile device. In another embodiment the SPU is an ECG interface module. The ECG signal may be received through a wireless connection, such as Bluetooth or Wi-Fi, and processed by the application processor (AP) of the mobile device according to blocks 902, 904, 906, 908, 910, 912, and 914. Regardless of the form factor of the SPU, portions of the processing of blocks 902, 904, 906, 908, 910, 912, and 914 may be offloaded to remote computer systems. For example, the R and P values may be determined by the SPU and then transmitted to a remote computer system with the machine-learning algorithm that performs the processing of block 914 and returns the determined location to the SPU. As another example, the SPU may receive the ECG signals at blocks 902 and 904 and then transmit the ECG signals to a remote computer system for processing at blocks 906, 908, 910, 912, and 914 to determine R-wave and P-wave peaks for the signals and determine the location of the catheter.

In some embodiments, a baseline (BL) ECG signal is used to normalize a live ECG signal for the particular patient receiving the catheter. In one embodiment, the BL signal may be obtained using a surface lead acquired at the beginning of a catheter insertion procedure to account for possible variations in the characteristics of the ECG signal among different patients. This recording may be obtained as shown in FIG. 10. FIG. 10 is an illustration of an example placement of leads on a neonate for recording a baseline ECG signal according to some embodiments of the disclosure. A negative electrode is connected at a top-right side of the baby at location 1002 for ten seconds, while a common electrode is placed on the neonate's left side of chest at location 1006 and a positive electrode is placed on the neonate's left leg at location 1004. In another embodiment, the BL signal may be obtained using ECG signals exported from bedside monitors connected to the patient. After the baseline ECG is obtained, a live ECG may be obtained using the configuration of FIG. 11. FIG. 11 is an illustration of an example placement of leads on a neonate for recording a live ECG signal according to some embodiments of the disclosure. For a live ECG recording, the lead of the catheter functions as a negative electrode 1104, while a common electrode is connected on the neonate's right side of the chest at location 1106 and a positive electrode is placed on the neonate's left leg at location 1102. In one embodiment of the disclosure, the BL ECG signal is the same as the L ECG signal. In such embodiments features of the live signal may be used to normalise the monitored ECG signals.

Figure 12:
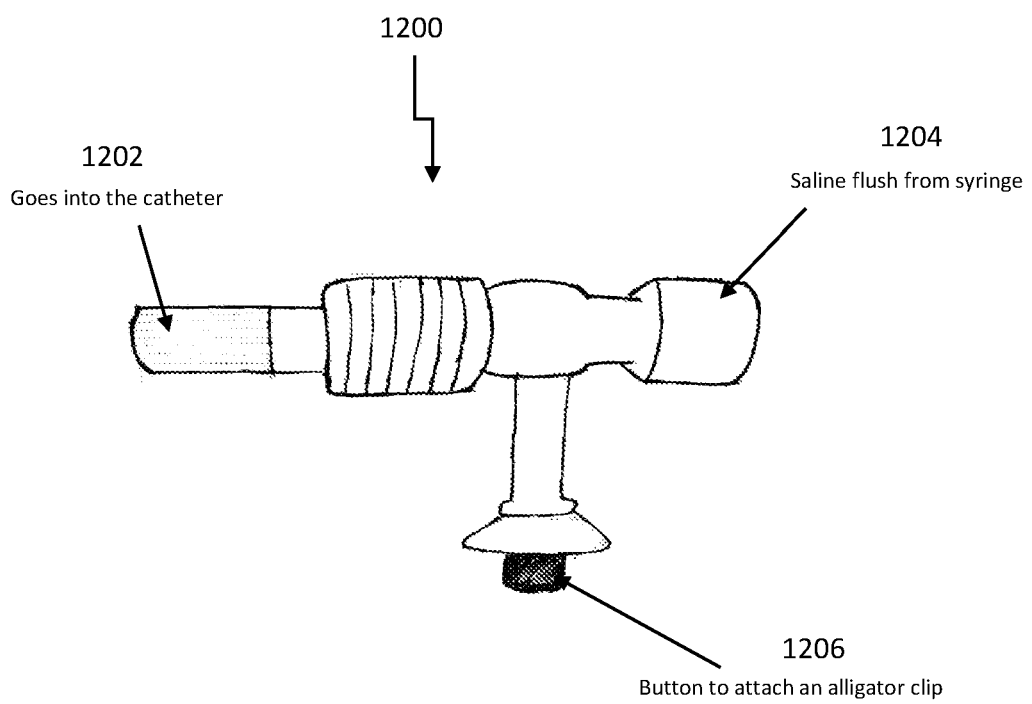
FIG. 12 is a side view of a catheter adapter for obtaining ECG signals from a catheter according to some embodiments of the disclosure.

The live ECG recordings may be recorded from the proximal end of a catheter using a catheter adapter, one example of which is shown in FIG. 12. FIG. 12 is a side view of a catheter adapter for obtaining ECG signals from a catheter according to some embodiments of the disclosure. A catheter adapter 1200 is a component that is attached to the proximal end of a standard catheter and can be used to establish a safe electrical connection between the patient and the SPU. The catheter adapter 1200 may have a three-way connection that accommodates a physical link between the catheter, a solution-flushing syringe—which includes but is not limited to saline, and a metallic (e.g. copper or gold) wire or other connection capable of electric signal transfer connected to the adapter through an alligator clip or other connection. When saline or other electrically conductive solution is flushed through opening 1204 to the catheter during a catherization procedure, the saline's or other solution's conductive nature creates an electrical connection between an electrical connection at location 1206 and the fluidic environment inside the vascular system. An opening 1202 extends to the catheter.

It should be appreciated that before the intravascular signal can be analysed for feature extraction and catheter location determination, a check should be performed to determine whether or not the IECG signal is of adequate quality for analysis. In a simple embodiment, confirming the IECG signal is being received maybe performed by displaying the received IECG for visual checking by the clinician. For example, if the IECG signal is absent then the clinician may inject more saline to see if the problem is resolved. However, such a visual check may not be sufficient to identify any artefacts in the signal with may cause problems during signal analysis. Before the analysis of the features of the IECG signal, it is important to make sure that the IECG signal is present and is sufficiently free of any artefacts as they can potentially lead to false positives and false negatives. Hence, prior to location prediction (aside from signal filtering), a quick test can be performed on the IECG data to determine the signal quality. The test involves performing a fast Fourier transform (FFT) on a sample of the IECG signal, for example 2-10 seconds, in an embodiment 5 seconds, to convert the signal to the frequency domain for analysis. The FFT can be performed using any known technique and such algorithms are commonly used. It should be noted that FFTs do not require any normalisation as a noised/absent signal is expected to appear significantly different to a normal signal in the frequency domain regardless of the patient or their age. The FFT can be analysed in the frequency domain to determine quality of the signal based on frequency response within a target expected range, centred around 3 Hz for a clean signal, very high frequency responses are characteristic of noisy signals. Where the FFT does not display the anticipated characteristics for a clean signal, an alert may be triggered to warn the clinician. If the problem is not resolved by increasing saline the clinician may choose to revert to conventional catheter tip location determination techniques.

The IECG signal quality check can be performed periodically during a catheterization procedure. For example, during the catheterization procedure, a unipolar intravascular ECG is captured via a saline column. The time window for the data capture depends on the clinician's preference and the use of the specific machine learning method. There are two such methods, one is called the classification method that requires the clinician to stop for two seconds after every cm to capture data and the other one is called the regression method that requires the clinician to move the catheter slowly without stopping. These methods are described in detail later. The time period for sampling may vary depending on clinician preference and patient age. For a neonate, a time window of minimum 2 seconds is large enough to monitor a sufficient number of ECG samples for location analysis mainly because the neonatal heartbeat is very high compared to an adult. For instance, a heart rate of 140 bpm can provide more than 4 P and R wave peaks in a 2 second time window. Once the IECG data is captured it is subject to FFT and feature extraction processing as described above. Each location determination during the procedure may include an initial step of checking the signal data quality before proceeding with location determination.

In one example, the FFT is analysed to calculate the maximum in the FFT array produced from the signal is passed onto a specialised machine learning derived classification model to determine the quality of the signal. In some embodiments the P/R data, for example P/R ratio (determined from feature extraction), may also be input to the quality determination, this P/R data may be from a preceding sample. For example, the machine learning engine 350 may include a signal quality determination module 352 utilising this model. The model can be derived by training either a support vector machine algorithm or a neural network architecture with ECG data that is specifically labelled with classes: 'clean', 'no signal', and 'noisy signal'. All these classes will have separation boundaries which will be represented as the function of the P/R ratio and the maximum of the signal FFT. Labelling of these signals can be based on the following expected characteristics: 1. A clean signal is expected to have a frequency response centred around 1 to 3 Hz and a non-zero P/R ratio 2. A noisy signal is expected to have a very high frequency component and depending on the signal presence P/R can either be zero/infinite or non-zero 3. An empty signal is expected to have a zero/infinite P/R. If the signal is empty or noisy, the clinician will be prompted via the device's UI to check the connections or inject saline and see if the issue resolves. In some embodiments the signal processing unit may be configured to suspend catheter tip location determination where the signal quality is inadequate. This is to avoid risks associated with misplacement due to the automated position determination outputting erroneous or inaccurate results. In such circumstances traditional catheter tip location techniques, such as using x-rays may be used by the clinician.

Once the quality of signal is deemed clean, the features are passed on to the location determination module 355 that predicts the catheter location based on modelled associations of locations with characteristics of P and R wave peaks. This module 355 uses P and R-wave peaks to determine final catheter locations. Like the previous step, the module 355 can be trained using a labelled ECG dataset. The labelling of the ECG dataset can be done via the corresponding chest x-rays however, for CVC procedures only peaks that correspond to the final catheter locations in different attempts of the procedure will typically have x-ray confirmed locations according to standard procedures. The remaining unlabelled peaks/features can be subjected to an unsupervised machine learning algorithm called K-means clustering. It is expected that each unique location in the vascular pathway based on P and R-wave peaks can be represented by a separate cluster. These locations can then be identified by non-linear interpolation of the labelled data as either a close match or the most likely nearby location.

An alternative approach towards labelling is to train the model with only the available labelled data and use the unlabelled data with the derived machine learning model to estimate their probabilities of belonging to a specific location label. A close match/nearby location can be obtained based on the likelihood of data-point being near a location in the body. Location labelling can be further refined by the help of an expert electrophysiologist. Once all the datapoints have a location label, they can then be used to train either a classification or a regression algorithm. The data classification and regression approaches correspond to different methods used to capture IECG data during the procedure requiring different action by the clinician during catheterisation. For the regression method the clinician is required to move the catheter slowly without stopping. For the classification method the clinician is required to stop for two seconds after each centimetre to capture the IECG data.

Figure 13:
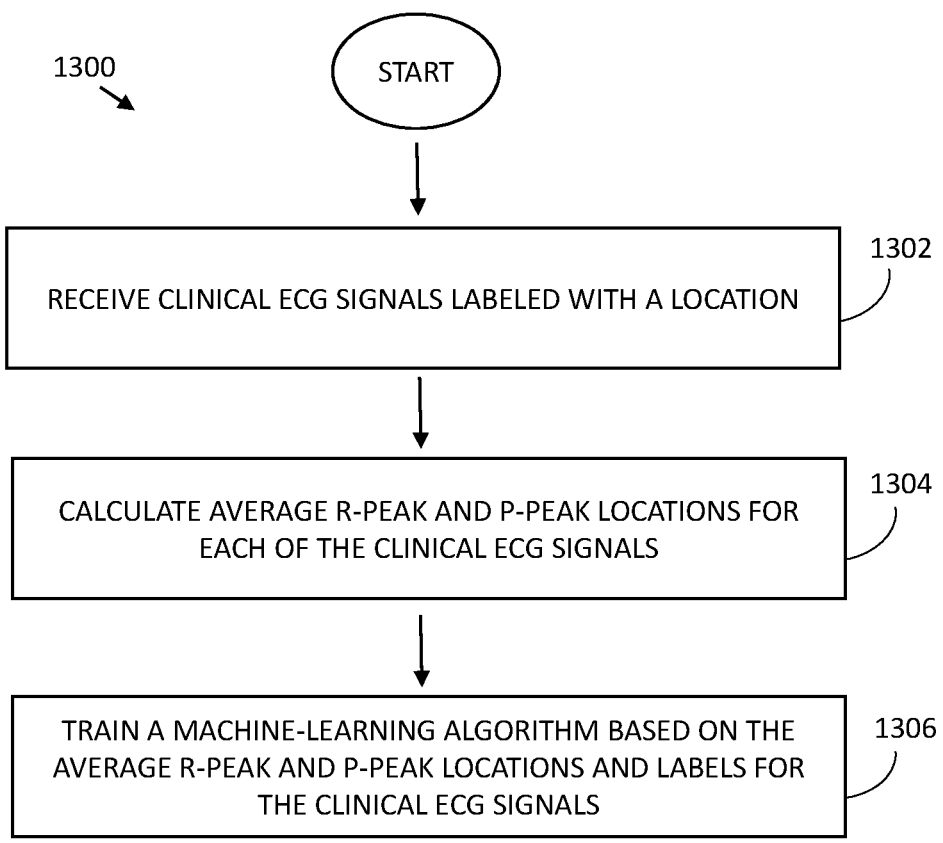
FIG. 13 is a flow chart illustrating an example method for training a machine-learning algorithm to determine catheter location based on an ECG signal according to some embodiments of the disclosure.
Figure 20A:
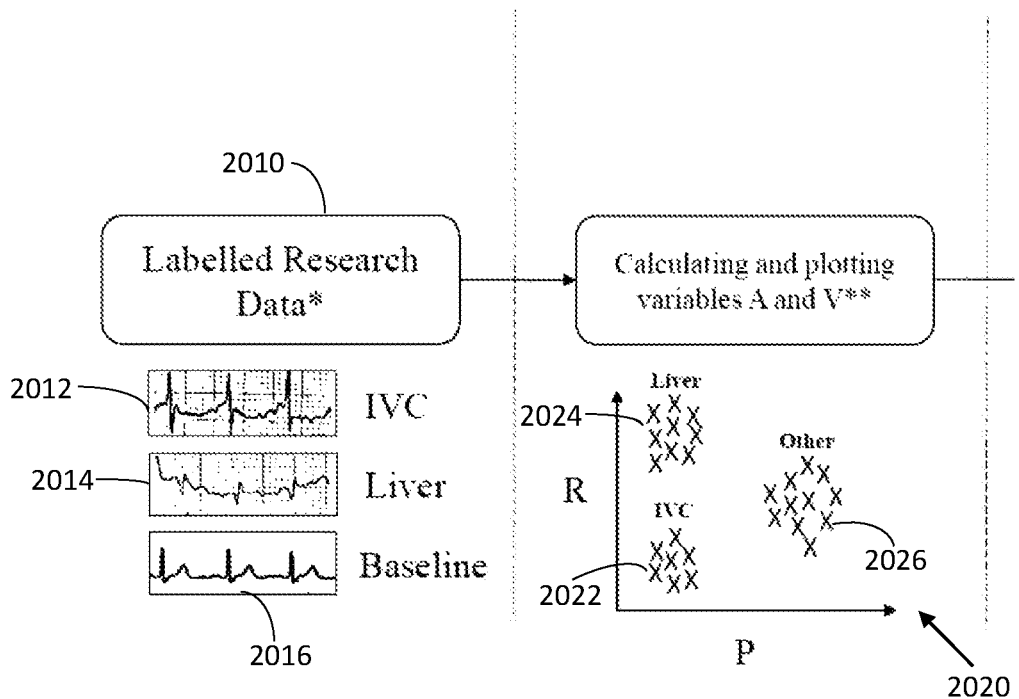
FIGS. 20a and b illustrates steps in a process of training a machine learning engine using a classification technique in accordance with some embodiments of the disclosure.
Figure 20B:
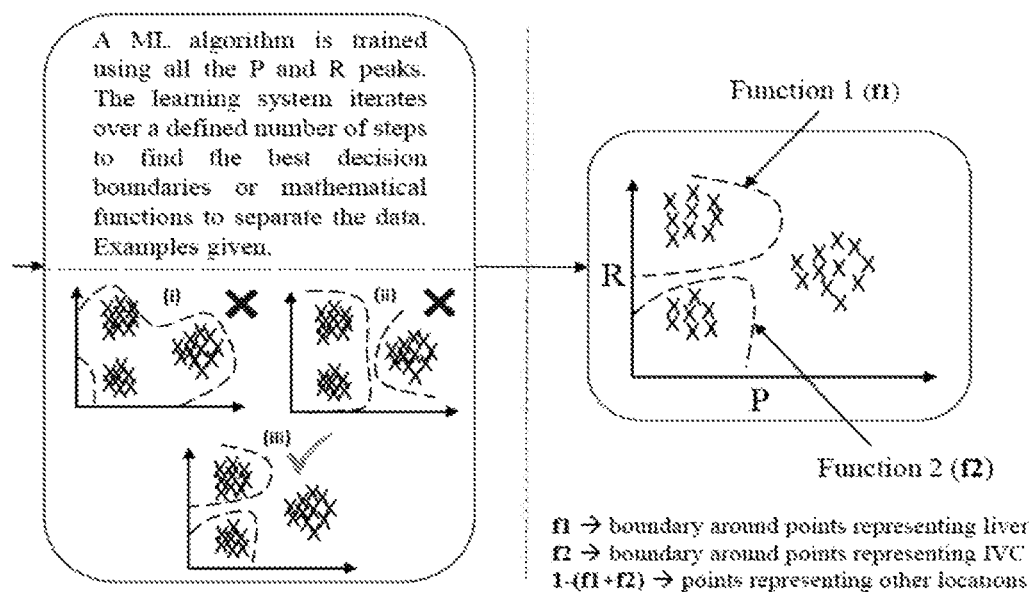

In some embodiments, a machine-learning algorithm is described for determining the location of the catheter during the catheterization procedure. The machine-learning algorithm may be trained using clinical data, including data obtained from human subjects, and/or animal subjects. In the data classification approach, the pre-processed (extracted and optionally normalised) features are subjected to classification learning algorithms such as Support Vector Machines (SVMs) or neural network with classification end layer to separate data points using their location with mathematical functions. The training of a classification model is further explained with reference to FIGS. 13 and 20. One example training process is illustrated in FIG. 13. FIG. 13 is a flow chart illustrating an example method for training a machine-learning algorithm to determine catheter location in UVC procedures based on an ECG signal according to some embodiments of the disclosure. A method 1300 begins at block 1302 with receiving clinical ECG signals labelled with a known location. The ECG signals block 1302 are recorded while the catheter is at a known location in the neonate, which may be determined with X-ray or ultrasound imaging during the catheterization procedure. FIG. 20 shows an example of the labelled research data 2010, which refers to ECG waveforms (from a UVC procedure) that are tagged with their original x-ray confirmed location. This example shows an ECG waveform for a correctly located catheter in the IVC (inferior vena cava) 2012, a catheter tip incorrectly located in the liver 2014 and a baseline ECG 2016, for example used for normalization. At block 1304, average R-peak and P-peak intensities are determined for the labelled clinical ECG signals using feature extraction methods as described above. After feature extraction P and R wave peak amplitudes (which may be normalized using the baseline ECG or may be simply averaged over a sample) are plotted 2020 and labelled. In this example, P and R represent normalised averaged P and R peaks for a particular location. As can be observed from the graph 2020 plots of P and R data for Liver 2024 and IVC 2022 are represented by their respective data clusters, and a third data cluster 2026 represents another location or locations. The machine learning algorithm is trained using all the labelled P and R peaks. At block 1306, the machine-learning algorithm is trained using the average R-peak and P-peak intensities and known location for those locations. The learning system iterates over a defined number of steps to find the best decision boundaries or mathematical functions to separate the data. In the example shown the outcome of the training is Function 1 (f1) defining a boundary around pointe representing the liver, function 2 (f2) defining a boundary around points representing the IVC, and the remaining points representing every other location (1−(f1+f2)). As additional samples are provided to the machine-learning algorithm at block 1306 the model for the algorithm can be updated.

Figure 14:
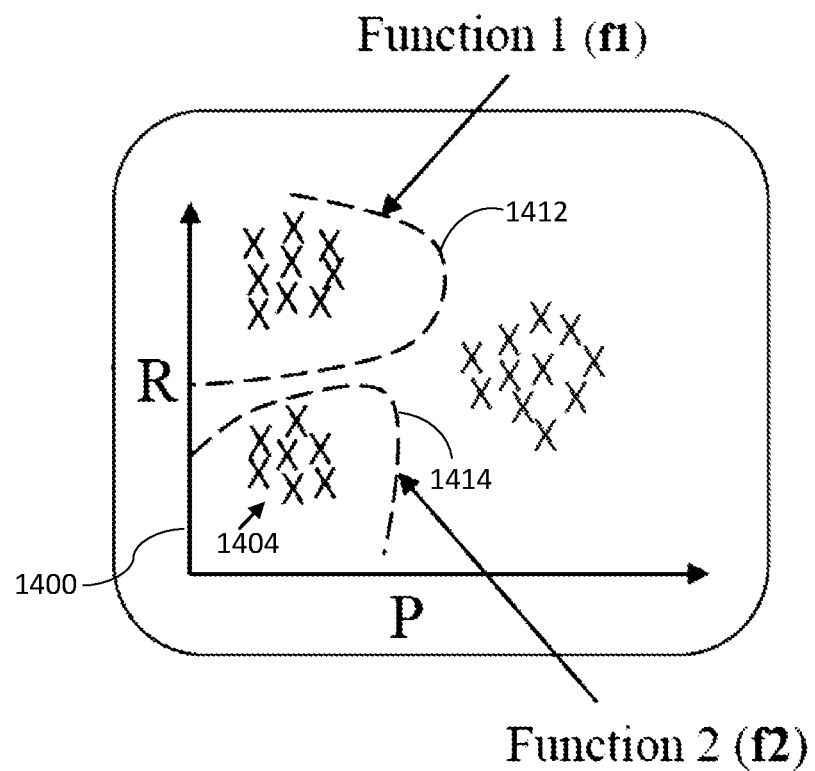
FIG. 14 is a graph illustrating example learned functions for catheter location according to some embodiments of the disclosure.
Figure 15:
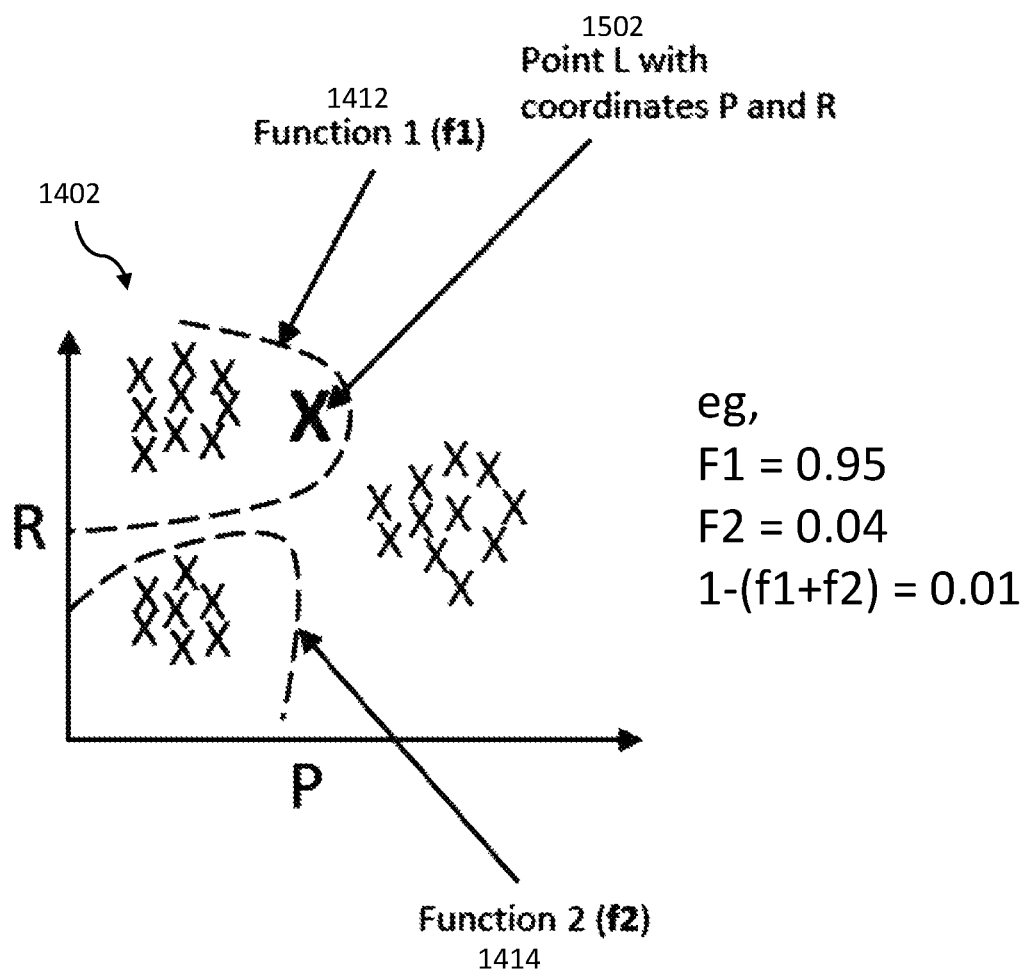
FIG. 15 is a graph illustrating an example determination of catheter location using learned functions according to some embodiments of the disclosure.

A walkthrough example of predicting the live catheter tip location in UVC procedures using the classification model for determining location of the catheter is shown in FIG. 14. FIG. 14 is a graph illustrating example learned functions for catheter location according to a classification model embodiment. A graph 1400 plots each (R, P) value from the labelled clinical ECG signals. Data 1402 are associated with locations near the liver. Data 1404 are associated with locations near the IVC. Function 1 (f1) 1412 of the model defines a boundary around (R, P) values corresponding to the liver location. Function 2 (f2) 1414 of the model defines a boundary around (R, P) values corresponding to the IVC location. When a live ECG signal is obtained and (R, P) values are determined, using feature extraction as described above, the location may be determined using the model of FIG. 14. An example of the determination is shown in FIG. 15. FIG. 15 is a graph illustrating an example determination of catheter location using learned functions according to some embodiments of the disclosure. In this example the liver is the location where the catheter is current stopped. A location L 1502 corresponds to P and R coordinates (for example, normalised averaged R and P wave peak amplitude values) for a live ECG signal. The model calculates the probability of the UVC tip being at the liver, IVC or any other location in the umbilical pathway, illustrated as f1 1412, f2 1414 and 1−(f1+f2) respectively, f1 and f2 are calculated as probabilities of point L 1502 being within their boundaries. The UVC is determined to be within the boundary of function f1 1412 belonging to the liver cluster due to this having the highest calculated probability. Thus, the trained machine-learning algorithm determines the location of the catheter to be in the liver with a 95% probability. The algorithm may also determine a 5% probability that the catheter is in the IVC.

Figure 21A:
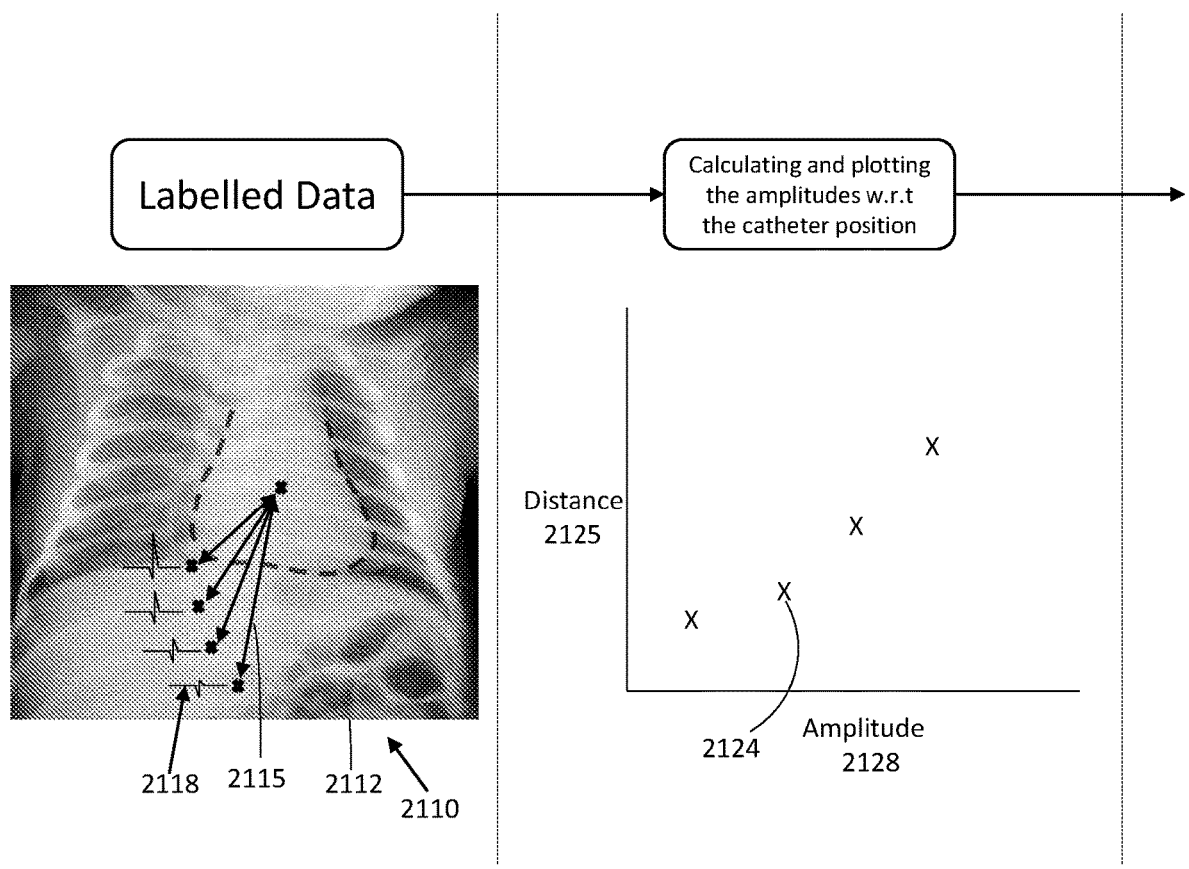
FIGS. 21a and b illustrates steps in a process of training a machine learning engine using a regression technique in accordance with some embodiments of the disclosure.
Figure 21B:
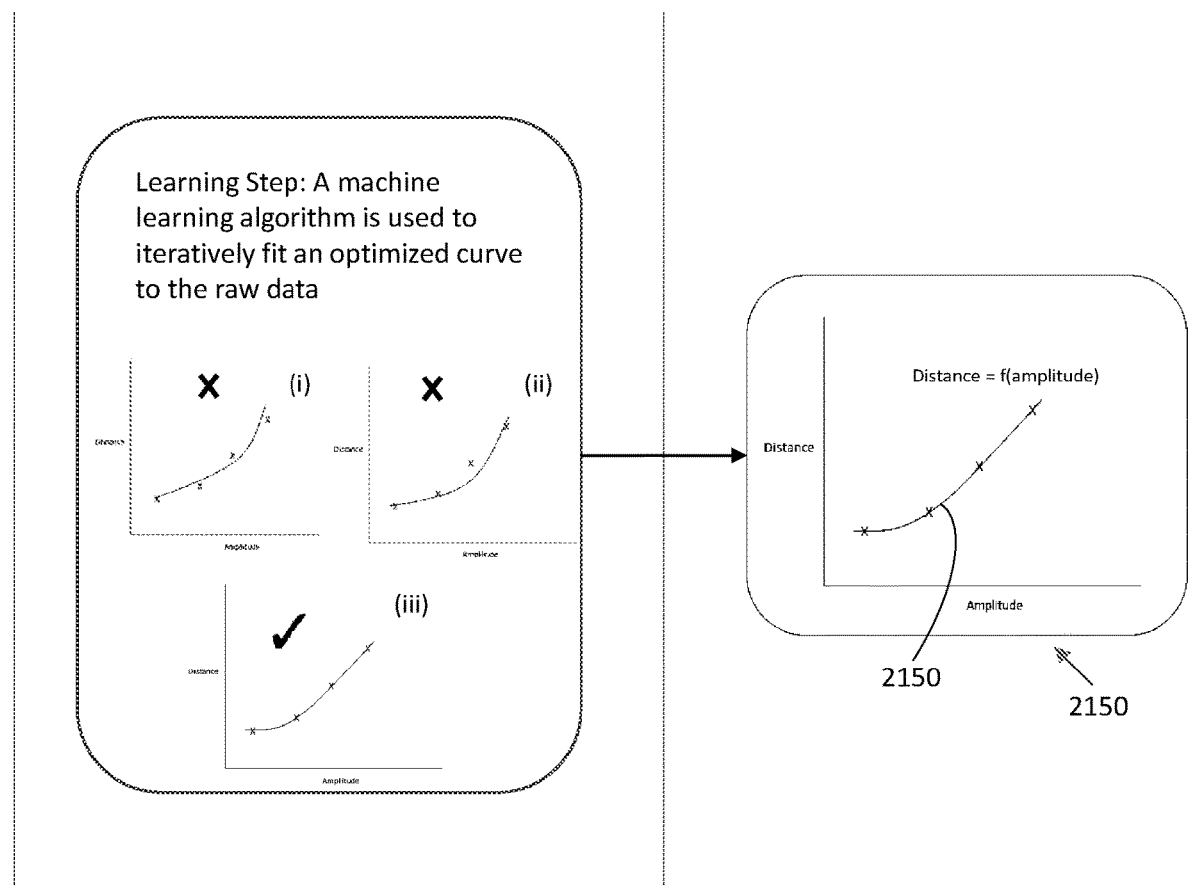
Figure 22A:
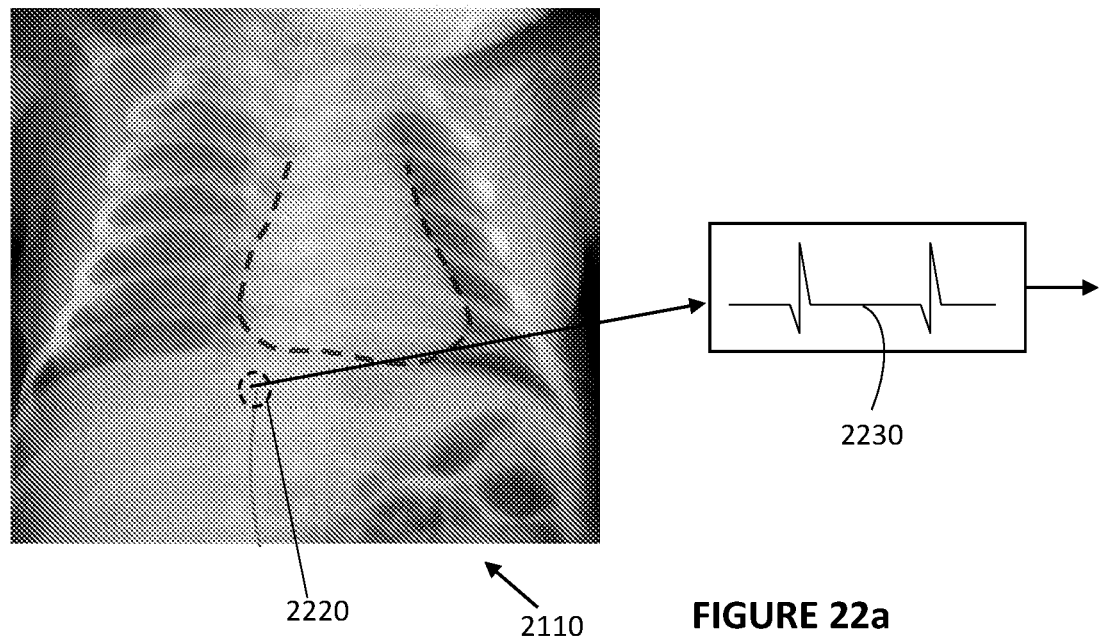
FIGS. 22a and b illustrates steps in a process or performing catheter tip location determination using a regression method trained machine learning engine in accordance with some embodiments of the disclosure.
Figure 22B:
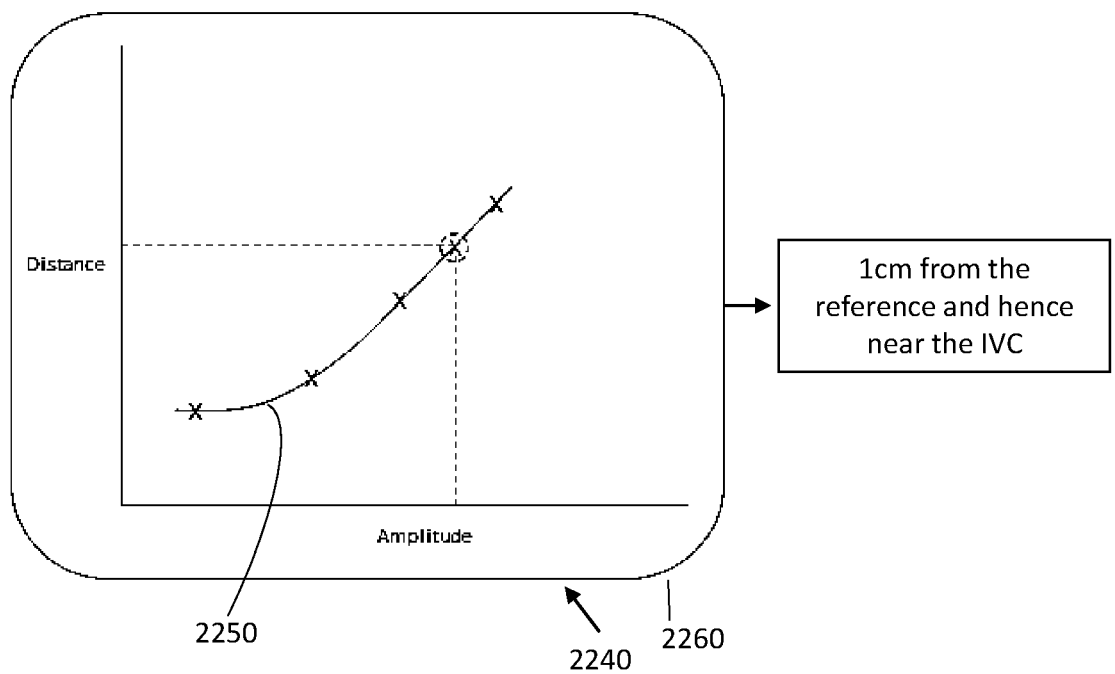

In the data regression approach, the labels assigned to the datapoints are quantitative catheter tip distances that are taken with respect to an anatomical reference point (such as the cardiac silhouette, diaphragm or a vertebra). These datapoints are plotted against the features and an optimised polynomial curve is fitted across it. The equation of the curve can then be used to predict the distance of the catheter tip with respect to the selected reference. The training of a regression model is explained with reference to FIG. 21. Data is extracted from an x-ray of a neonate during a UVC procedure 2110 by selecting the centroid 2112 of the cardiac silhouette as the reference point 2112. Distance 2115 calculated from the reference 2112 is assigned to each ECG waveform 2118 captured through the catheter tip at that point. The peak amplitudes 2128 (in FIGS. 21 P and R simplified to a single peak 2124 for illustration, plots for both R and P peaks may be used) from the waveforms 2124 are plotted 2120 against these distance 2125 values and a curve 2150 is fitted on the data using a machine learning algorithm. The final model 2140 can now be used to predict the distances (which represent the catheter location in the x-ray with reference to the cardiac silhouette) using the peak amplitudes. It should be appreciated that the regression model can include multiple curves representing different regions and representing both R and P peaks. A walkthrough example of predicting the live catheter tip location during UVC procedures using the regression model is given with reference to FIG. 22. In this example an x-ray 2210 is shown where the catheter 2220 is just below the IVC. The acquired ECG signal 2230 has its peak amplitude extracted (and normalised). The peaks are then used with previously trained regression model 2240 to predict the distance from the cardiac silhouette. This is done by determining, based on the peak amplitude values, a position on the curve 2250, for this position on the curve the distance to the reference point 2112 can be determined. The distance can then be used to determine the anatomical location of the catheter tip.

After the catheterisation procedure the patient will typically continue to be monitored and while the catheter remains inserted, the above methods may be used to continually or periodically determine the catheter tip location to monitor for migration of the catheter tip away from the target location. It should be appreciated that such ongoing monitoring may be largely automated. The signal processing system 104 may remain connected to continue to receive and monitor the intravascular ECG and optional surface ECG signals, and automatically perform catheter tip location determination, continually or periodically—controllable by a clinician using user settings. Where the catheter tip is determined to have migrated from the target location the system can be configured to output an alert via the user interface 106 alert module 390. For example, the alert may be an audible alert, change of display colour or other visual alert, the alert may also include a signal transmitted to central supervision station equipment, or to one or more mobile devices, for example carried by members of the clinical team and optionally one or more parents or careers. The automated and minimal intervention nature of the catheter tip location determination methods described above are advantageous for long term catheter tip migration monitoring.

Figure 16:
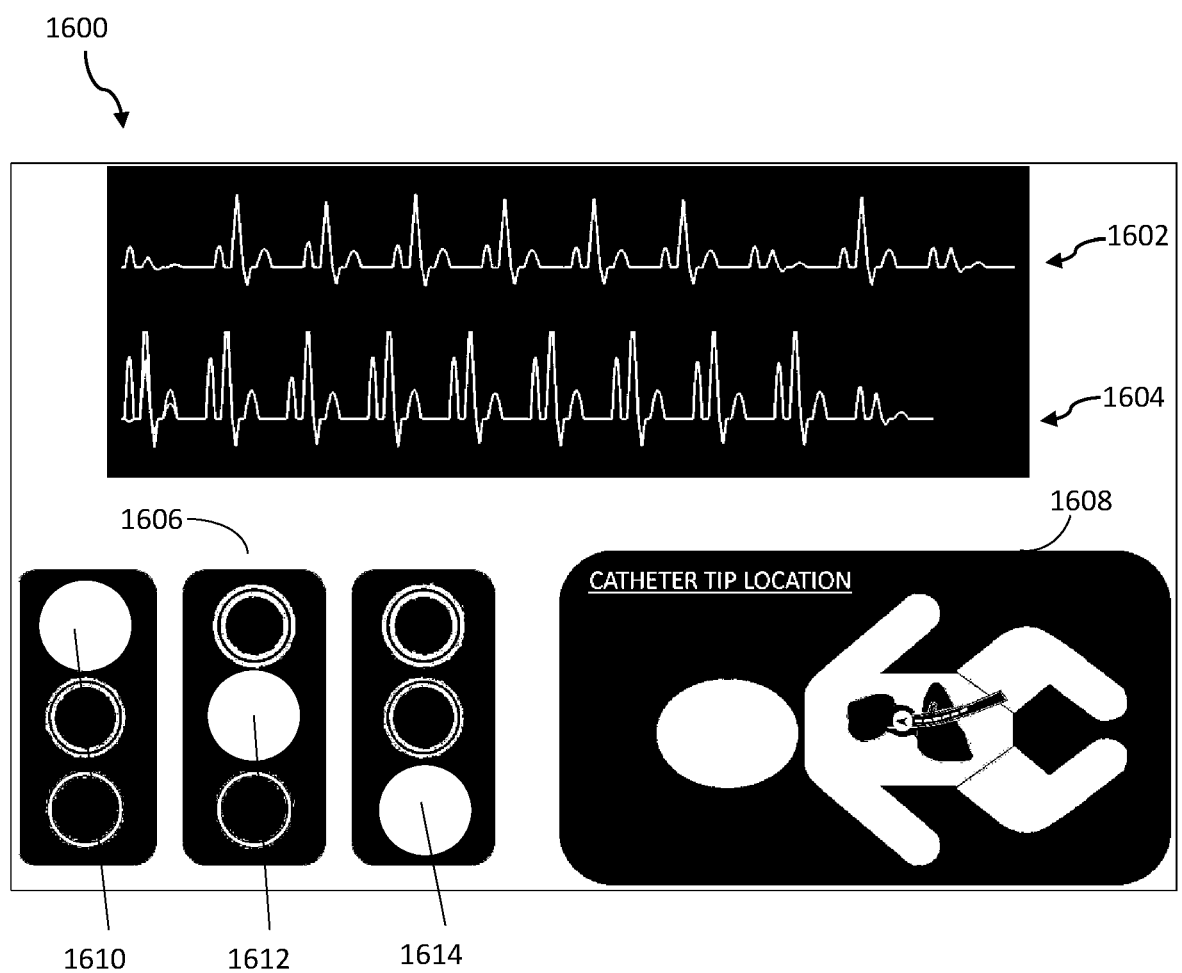
FIG. 16 is a user interface illustrating an example display for providing catheter location information to a user according to some embodiments of the disclosure.

The location determined using techniques of the embodiments described above may be output to a user through a user interface. One example user interface is shown in FIG. 16. FIG. 16 is a user interface illustrating an example display for providing catheter location information to a user according to some embodiments of the disclosure. A software window 1600 may be displayed on a personal computer or mobile device and include an output of a live ECG signal 1602, a baseline ECG signal 1604, a plurality of colors 1606 (for example red 1610, yellow 1612, green 1614), an illustration of a paediatric patient 1608, and/or a plurality of shapes (for example each different colour 1610, 1612, 1614 may be displayed having a different shape to enable easy differentiation even if one cannot distinguish colours) with the catheter position indicated. The plurality of colours 1606 may indicate the quality of the ECG signal and whether the catheter is in a correct final position, whether the catheter is in an incorrect final location, and/or whether the catheter is in neither a correct nor incorrect final location (such as if the catheter is advancing towards the correct final location). An example final target location may be the inferior vena cava (IVC) at, or just above, the level of the diaphragm, other target locations may also be used, such as in the lower third of the superior vena cava. Incorrect final locations include (but are not limited to) the right atrium (or further) or in the liver silhouette (e.g., liver vessel). A red light may be used to indicate an incorrect final location; a green light may be used to indicate a correct final location; and a blue light may be used to indicate neither an incorrect or correct final location. The window 1600 may include the catheter's absolute location, and also location as it relates to the path the catheter takes within the blood vessels with some vessels (such as umbilical vein and artery and the ductus venosus) and their relationship to each other being unique to the neonate. The window 1600 may also include general vascular anatomy as well allow for display of the unique vascular anatomy of the paediatric patient (including relevant anatomy as it relates to placement and the risk of misplacement of catheters).

Figure 23:
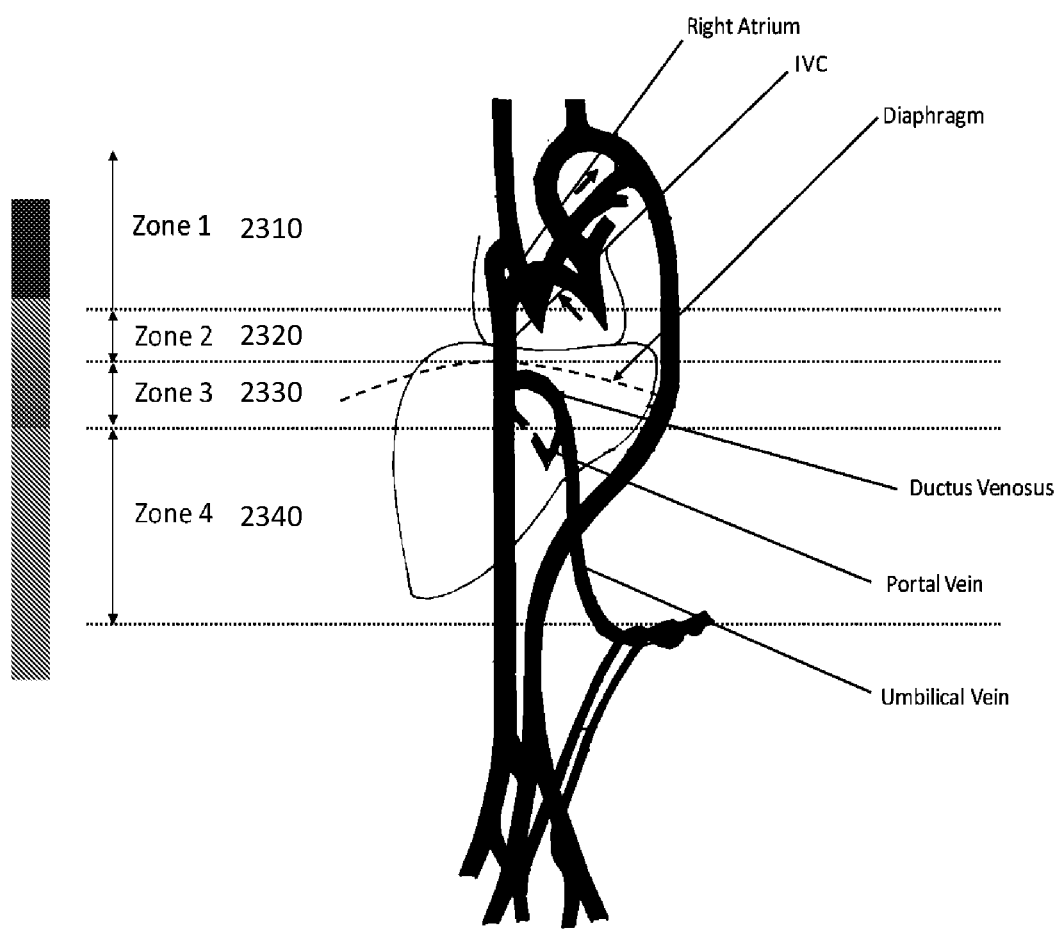
FIG. 23 illustrates and example of zone-based catheter location indication display in accordance with some embodiments of the disclosure.

In another example displaying the location of the catheter includes determining a catheter location zone and displaying zone indication. An example of zones for UVC procedures is shown in FIG. 23, where Zone 4 2340 is when the catheter is in the umbilical vein, but has not passed through the ductus venosus (sub-optimal location & too low, Zone 3 2330 is when the catheter is passed the ductus venosus, but has not reached the level of the IVC (sub-optimal location & too low), Zone 2 2320 is when the catheter is in the optimal location of the IVC (optimal location), and Zone 1 2310 is when the catheter is too far into the right atrium and has passed the IVC (sub-optimal location & too high). Each of these zones have distinct signals when looking at the P and R peaks of the ECG waveform. These zones can be utilised for display and visual indication of catheter tip location in conjunction with any of above described location determination methods.

Although a software interface is described for outputting the determined location of the catheter, other types of feedback mechanisms may be used to provide information to a user during the catherization procedure and while the catheter is inserted. For example, a plurality of light emitting diodes (LEDs) may be configured to output the red, green, and blue light described above. As another example, audible feedback may be provided to the user, such as by increasing or decreasing a rate of a beeping noise while the catheter is being advanced to the correct final location. Other sounds may be output if the catheter reaches a correct or incorrect final location. As yet another example, tactile feedback may be provided to the user, such as by lightly vibrating the catheter adapter when the catheter reaches a correct final location. Force feedback devices may alternatively be used to provide tactile feedback to a user's gloves or another connected device such as a cellular phone.

The operations described above as performed by a signal processing unit may be performed by any circuit configured to perform the described operations. Such a circuit may be an integrated circuit (IC) constructed on a semiconductor substrate and include logic circuitry, such as transistors configured as logic gates, and memory circuitry, such as transistors and capacitors configured as dynamic random access memory (DRAM), electronically programmable read-only memory (EPROM), or other memory devices. The logic circuitry may be configured through hard-wire connections or through programming by instructions contained in firmware or software stored in the memory. Further, the logic circuitry may be configured as a general-purpose processor (e.g., CPU or DSP) capable of executing instructions contained in software. The firmware and/or software may include instructions that cause the processing of signals described herein to be performed. The circuitry or software may be organized as blocks that are configured to perform specific functions. Alternatively, some circuitry or software may be organized as shared blocks that can perform several of the described operations.

If implemented in firmware and/or software, functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise random access memory (RAM), read-only memory (ROM), electrically-erasable programmable read-only memory (EEPROM), compact disc read-only memory (CD-ROM) or other optical disk storage, magnetic disk storage or other magnetic storage devices, solid state memory device (i.e. USB stick) or any other medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

The described methods are generally set forth in a logical flow of steps. As such, the described order and labeled steps of representative figures are indicative of aspects of the disclosed method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagram, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Although the present disclosure and certain representative advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. For example, although certain algorithms for determining characteristics of the ECG signal, such as peak locations, are described, other algorithms may be used to determine the location of the catheter. As another example, although certain functions for determining a location of the catheter are described and use certain values as inputs, other functions based on other values may be used to determine the location. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. A machine learning engine, comprising:
   a signal quality determination module trained to determine signal qualities of intravascular electrocardiogram (ECG) signals from a tip of a catheter inserted in a patient as clean, no signal, and noisy signal,
   the determination based on a frequency response of the intravascular ECG signals and P/R ratios determined from feature extraction from the intravascular ECG signals, and
   the signal quality determination module being previously trained using a set of pre-recorded intravascular ECG tracings labelled with signal qualities comprising clean, no signal, and noisy signal; and
   a location determination module trained to determine a relative location of the tip of the catheter in the patient based on modelled associations of locations with characteristics of P-wave and R-wave peaks extracted from the intravascular ECG signals,
   the characteristics of P-wave and R-wave peaks comprising one or more of:
      a P/R ratio of the averaged P-wave and R-wave peaks, and
      normalised averaged P-wave and R-wave peaks, each normalization obtained by a ratio between an averaged surface ECG P-wave peak and an averaged intravascular P-wave peak or an averaged surface ECG R-wave peak and an averaged intravascular R-wave peak, respectively, and the surface ECG peaks being captured prior to receiving the intravascular ECG signals, and
   the location determination module being previously trained using a set of pre-recorded intravascular ECG tracings obtained from catheters and labelled with the known locations of the catheters in patients' bodies,
   wherein the signal quality determination module is configured to pass the intravascular ECG signals to the location determination module if they are determined to have a clean signal quality.

2. The machine learning engine of claim 1, wherein the signal quality determination module is further configured to generate an alert if the intravascular ECG recordings are determined to have a noisy or empty signal quality.

3. The machine learning engine of claim 1, wherein the machine learning engine uses at least one of an artificial neural network algorithm, a deep learning algorithm, a Bayesian network algorithm, a decision tree learning algorithm, and a rule-based learning algorithm.

4. A machine learning method, comprising:
   receiving intravascular electrocardiogram (ECG) signals from a tip of a catheter inserted in a patient;
   inputting the intravascular ECG signals to a machine learning engine comprising a signal quality determination module and a location determination module,
      wherein the signal quality determination module is trained to determine signal qualities of the intravascular ECG recordings as clean, no signal, and noisy signal,
      the determination based on a frequency response of the intravascular ECG signals and P/R ratios determined from feature extraction from the intravascular ECG signals,
      the signal quality determination module being previously trained using a set of pre-recorded intravascular ECG tracings labelled with signal qualities comprising clean, no signal, and noisy signal,
      wherein the location determination module is trained to determine a relative location of the tip of the catheter in the patient based on modelled associations of locations with characteristics of P-wave and R-wave peaks extracted from the intravascular ECG signals,
      the characteristics of P-wave and R-wave peaks comprising one or more of:
         a P/R ratio of the averaged P-wave and R-wave peaks, and
         normalised averaged P-wave and R-wave peaks, each normalization obtained by a ratio between an averaged surface ECG P-wave peak and an averaged intravascular P-wave peak or an averaged surface ECG R-wave peak and an averaged intravascular R-wave peak, respectively, and the surface ECG peaks being captured prior to receiving the intravascular ECG signals, and
      the location determination module being previously trained using a set of pre-recorded intravascular ECG tracings obtained from catheters and labelled with the known locations of the catheters in patients' bodies; and
   passing the intravascular ECG signals determined to have a clean signal quality from the signal quality determination module to the location determination module.

5. The machine learning method of claim 4, wherein the signal quality determination module is further configured to generate an alert if the intravascular ECG recordings are determined to have a noisy or empty signal quality.

6. The machine learning method of claim 4, wherein the machine learning engine uses at least one of an artificial neural network algorithm, a deep learning algorithm, a Bayesian network algorithm, a decision tree learning algorithm, and a rule-based learning algorithm.

* * * * *